US009994824B2

(12) United States Patent
Sung

(10) Patent No.: US 9,994,824 B2
(45) Date of Patent: Jun. 12, 2018

(54) METHOD FOR PROMOTING HAIR GROWTH USING COMPOSITION COMPRISING PDGF-D TREATED ADIPOSE-DERIVED STEM CELLS

(71) Applicant: INDUSTRY-ACADEMIC COOPERATION FOUNDATION, YONSEI UNIVERSITY, Seoul (KR)

(72) Inventor: Jong Hyuck Sung, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 94 days.

(21) Appl. No.: 15/090,542

(22) Filed: Apr. 4, 2016

(65) Prior Publication Data
US 2016/0289641 A1 Oct. 6, 2016

(30) Foreign Application Priority Data

Apr. 3, 2015 (KR) .................. 10-2015-0047766

(51) Int. Cl.
C12N 5/0775 (2010.01)
A61K 35/28 (2015.01)
A61K 8/98 (2006.01)
A61Q 7/00 (2006.01)

(52) U.S. Cl.
CPC ............ *C12N 5/0667* (2013.01); *A61K 8/981* (2013.01); *A61K 35/28* (2013.01); *A61Q 7/00* (2013.01); *C12N 2501/135* (2013.01)

(58) Field of Classification Search
CPC combination set(s) only.
See application file for complete search history.

(56) References Cited

FOREIGN PATENT DOCUMENTS

WO    WO 10/002846    *    1/2010    ............... C12N 5/06

OTHER PUBLICATIONS

Park et al, "Hair Growth stimulated by conditioned medium of adipose-derived stem cells is enhanced by hypoxia: evidence of increased growth factor secretion". Biomedical Research, 2010, vol. 31, No. 1, pp. 27-34. (Year: 2010).*
Sotoca et al, "Comparative proteome approach demonstrates that platelet-derived growth factor C and D efficiently induce proliferation while maintaining pluripotency of hMSCs" Experimental Cell Research, ePub: Aug. 9, 2013, vol. 319, pp. 2649-2662. (Year: 2013).*
Kim et al., "Antiwrinkle effect of adipose-derived stem cell: Activation of dermal fibroblast by secretory factors", Journal of Dermatological Science, 2009, vol. 53, pp. 96-102.
Altman et al., "IFATS Collection: Human Adipose-Derived Stem Cells Seeded on a Silk Fibroin-Chitosan Scaffold Enhance Wound Repair in a Murine Soft Tissue Injury Model", Stem Cells, 2009, vol. 27, pp. 250-258.
Won et al., "Hair growth promoting effects of adipose tissue-derived stem cells", Journal of Dermatological Science, 2010, vol. 57, pp. 134-137.
Kim et al., "The Molecular Mechanism Underlying the Proliferating and Preconditioning Effect of Vitamin C on Adipose-Derived Stem Cells", Stem Cells and Development, 2014, vol. 23, No. 12, pp. 1364-1376.
Festa et al., "Adipocyte lineage cells contribute to the skin stem cell niche to drive hair cycling", Cell, Sep. 2, 2011, vol. 146, No. 5, pp. 761-771.
Tomita et al., "PDGF isoforms induce and maintain anagen phase of murine hair follicles", Journal of Dermatological Science, 2006, vol. 43, pp. 105-115.
Andrae et al., "Role of platelet-derived growth factors in physiology and medicine", Genes & Development, 2008, vol. 22, pp. 1276-1312.
Hoch et al., "Roles of PDGF in animal development", Development, 2003, vol. 130, pp. 4769-4784.
Hannink et al., "Structure and function of platelet-derived growth factor (PDGF) and related proteins", Biochimica et Biophysica Acta, 1989, vol. 989, pp. 1-10.
Heldin, "Structural and functional studies on platelet-derived growth factor", The EMBO Journal, 1992, vol. 11, No. 12, pp. 4251-4259.
Demoulin et al., "PDGF receptor signaling networks in normal and cancer cells", Cytokine & Growth Factor Reviews, 2014, vol. 25, pp. 273-283.
Levitzki, "PDGF receptor kinase inhibitors for the treatment of PDGF driven diseases", Cytokine & Growth Factor Reviews, 2004, vol. 15, pp. 229-235.
Blazevic et al., "12/15-Lipoxygenase Contributes to Platelet-derived Growth Factor-induced Activation of Signal Transducer and Activator of Transcription 3", The Journal of Biological Chemistry, Dec. 6, 2013, vol. 288, No. 49, pp. 35592-35603.
Shimizu et al., "ROS and PDFG-β receptors are critically involved in indoxyl sulfate actions that promote vascular smooth muscle cell proliferation and migration", Am J Physiol Cell Physiol, 2009, vol. 297, pp. C389-C396.
Lange et al., "Platelet-derived growth factor BB stimulates vasculogenesis of embryonic stem cell-derived endothelial cells by calcium-mediated generation of reactive oxygen species", Cardiovascular Research, 2009, vol. 81, pp. 159-168.
Bergsten et al., "PDGF-D is a specific, protease-activated ligand for the PDGF b-receptor", Nature Cell Biology, May 2001, vol. 3, pp. 512-516.
Larochelle et al., "PDGF-D, a new protease-activated growth factor", Nature Cell Biology, May 2001, vol. 3, pp. 517-521.

(Continued)

*Primary Examiner* — Allison M Fox
(74) *Attorney, Agent, or Firm* — Knobbe Martens Olson & Bear LLP

(57) ABSTRACT

Provided is a composition for promoting hair growth comprising platelet-derived growth factor-D (PDGF-D)-treated adipose-derived stem cells (ASCs) as an active ingredient, and more particularly, a therapeutic agent for hair loss comprising ASCs with increased proliferation and migration by PDGF-D and increased expression and secretion of a growth factor as an active ingredient. PDGF-D-treated ASCs have improved hair regenerative potential through the increases in proliferation, migration and growth factor secretion and thus are useful for a therapeutic agent for hair loss or a cosmetic for preventing hair loss.

6 Claims, 27 Drawing Sheets

(56) References Cited

OTHER PUBLICATIONS

Li et al., "PDGF-D is a potent transforming and angiogenic growth factor", Oncogene, 2003, vol. 22, pp. 1501-1510.
Sun et al., "PDGF-BB-induced MT1-MMP expression regulates proliferation and invasion of mesenchymal stem cells in 3-dimensional collagen via MEK/ERK1/2 and PI3K/AKT signaling", Cellular Signalling, 2013, vol. 25, pp. 1279-1287.
Ball et al., "Platelet-derived growth factor receptor-X is a key determinant of smooth muscle X-actin filaments in bone marrow-derived mesenchymal stem cells", The International Journal of Biochemistry & Cell Biology, 2007, vol. 39, pp. 379-391.
Najy et al., "Differential Tumorigenic Potential and Matriptase Activation between PDGF B versus PDGF D in Prostate Cancer", Mol Cancer Res., Aug. 2012, vol. 10, No. 8, pp. 1087-1097.
Ball et al., "Inhibition of Platelet-Derived Growth Factor Receptor Signaling Regulates Oct4 and Nanog Expression, Cell Shape, and Mesenchymal Stem Cell Potency", Stem Cells, 2012, vol. 30, pp. 548-560.
Ball et al., "Vascular endothelial growth factor can signal through platelet-derived growth factor receptors", The Journal of Cell Biology, May 7, 2007, vol. 177, No. 3, pp. 489-500.
Kang et al., "Role of c-Jun N-terminal Kinase in the PDGF-Induced Proliferation and Migration of Human Adipose Tissue-Derived Mesenchymal Stem Cells", Journal of Cellular Biochemistry, 2005, vol. 95, pp. 1135-1145.
Kim et al., "Reactive oxygen species-responsive miR-210 regulates proliferation and migration of adipose-derived stem cells via PTPN2", Cell Death and Disease, 2013, vol. 4, e588.
Devarajan et al., "Epithelial-mesenchymal transition in breast cancer lines is mediated through PDGF-D released by tissue-resident stem cells", International Journal of Cancer, 2012, vol. 131, pp. 1023-1031.
Kim et al., "Hypoxia induces adipocyte differentiation of adipose-derived stem cells by triggering reactive oxygen species generation", Cell Biology International, 2014, vol. 38, pp. 32-40.
Song et al., "Variations of Clonal Marrow Stem Cell Lines Established from Human Bone Marrow in Surface Epitopes, Differentiation Potential, Gene Expression, and Cytokine Secretion", Stem Cells and Development, 2008, vol. 17, pp. 451-461.
Kim et al., "Primary Involvement of NADPH Oxidase 4 in Hypoxia-Induced Generation of Reactive Oxygen Species in Adipose-Derived Stem Cells", Stem Cells and Development, 2012, vol. 21, No. 12, pp. 2212-2221.
Kim et al., "The Pivotal Role of Reactive Oxygen Species Generation in the Hypoxia-Induced Stimulation of Adipose-Derived Stem Cells", Stem Cells and Development, 2011, vol. 20, No. 10, pp. 1753-1761.
Migliaccio et al., "The p66shc adaptor protein controls oxidative stress response and life span in mammals", Nature, Nov. 18, 1999, vol. 402, pp. 309-313.
Nemoto et al., "Redox Regulation of Forkhead Proteins Through a p66shc-Dependent Signaling Pathway", Science, Mar. 29, 2002, vol. 295, pp. 2450-2452.
Press release from Korean Ministry of Science, ICT and Future Planning, "Discovery of Growth Factor for Promoting Hair Growth and Regulating Functions of Adipose-Derived Stem Cells", Oct. 9, 2014.
Kim et al., "Functional Regulation of Adipose-Derived Stem Cells by PDGF-D", Stem Cells, 2015, vol. 33, pp. 542-556, Published online Oct. 21, 2014.

* cited by examiner

METHOD FOR PROMOTING HAIR GROWTH USING COMPOSITION COMPRISING PDGF-D TREATED ADIPOSE-DERIVED STEM CELLS

CROSS-REFERENCE TO RELATED APPLICATION

This application claims priority to and the benefit of Korean Patent Application No. 10-2015-0047766, filed on Apr. 3, 2015, the disclosure of which is incorporated herein by reference in its entirety.

BACKGROUND

1. Field

The present disclosure relates to a composition for promoting hair growth, or a therapeutic agent for hair loss.

2. Discussion of Related Technology

In addition to adipocytes, an adipose tissue is composed of microvessel endothelial cells, fibroblasts, myocytes, preadipocytes, etc. and is recently receiving attention since differentiation of mesenchymal stem cells into various tissues such as cartilages, bones, muscles and fats in a suitable environment has been reported. Recently, ASCs are applied to various fields for tissue regeneration and disease treatment, and particularly, since a large number of stem cells may be obtained from ASCs, compared to bone marrow or cord blood-derived mesenchymal stem cells, there is active clinical application of ASCs for skin, plastic surgery and beauty. Uncultured ASC extract fractions are clinically used in dermatology, plastic surgery, etc., and recently, a cellular therapeutic agent used for Crohn's disease has been approved.

ASCs are a type of mesenchymal stem cells that exhibit wound healing and antiaging effects on skin (Kim et al., *J Dermatol Sci* 53:96-102, 2009; Altman et al., *Stem Cells* 27:250-258, 2009). Recently, it was confirmed that the hair cycle of a mouse is shifted from telogen to an antigen phase due to ASCs pretreated with hypoxia or vitamin C (Won et al., *J Dermatol Sci* 57:134-137, 2010; Kim et al., *Stem Cells Dev* 23:1364-1376, 2014), which is caused by enhancing the hair regenerative potential of ASCs. As a growth factor expressed from ASCs and secreted, PDGF-A regulates the activity of hair follicular stem cells and induces the anagen of a hair cycle (Festa et al., *Cell* 146:761-771, 2011). In addition, injection of recombinant PDGF-A and B induces the anagen of murine hair follicles (Tomita et al., *J Dermatol Sci* 43:105-115, 2006).

PDGF is one of the growth factors that regulate cell growth and division (Andrae et al., *Genes Dev* 22:1276-1312, 2008; Kim et al., *Development* 130:4769-4784, 2003) and, as a mitogenic substance in an early developmental stage, affects the proliferation and migration of undifferentiated mesenchymal stem cells and some progenitor cells (Hannink et al., *Biochim Biophys Acta* 989:1-10, 1989; Heldin et al., *EMBO J* 11:4251-4259, 1992). In a later morphogenetic stage, PDGF signals are involved in tissue remodeling and cellular differentiation and play an important role in blood vessel formation. A PDGF signaling network includes four ligands such as PDGF-A, -B, -C and -D and two tyrosine kinase receptors such as PDGFR-α and PDGFR-β (Demoulin J B et al., *Cytokine Growth Factor Rev* 25:273-283, 2014; Levitzki A et al., *Cytokine Growth Factor Rev* 15:229-235, 2004). All PDGFs may form homodimers linked by a disulfide bond, and PDGF-A and -B may form heterodimers. When dimerized PDGFRs are activated, cytoplasmic domains are phosphorylated, and thus signal transduction is activated by the PI3K pathway or ROS generation (Blazevic T et al., *J Biol Chem* 288:35592-35603, 2013; Shimizu H et al., *Am J Physiol Cell Physiol* 297: C389-396, 2009; Lange S et al. *Cardiovasc Res* 81:159-168, 2009). PDGF-C and -D are recently found and bind with PDGFR-α and PDGFR-β, respectively (Bergsten E et al. *Nat Cell Biol* 3:512-516, 2001; LaRochelle W J et al., *Nat Cell Biol* 3:517-521, 2001). PDGF-D only forms homodimers and does not dimerize with the other three types of PDGFs. Also, PDGF-D is known to induce cell transformation and promote tumor growth (Li H et al., *Oncogene* 22:1501-1510, 2003).

In terms of the mitogenic effect of PDGFs on the mesenchymal stem cells, PDGF-B is known to regulate proliferation and invasion through the ERK and Akt signaling pathways (Sun X et al., *Cell Signal* 25:1279-1287, 2013), and PDGFR-α is known to be involved in formation of smooth muscle actin filaments in the mesenchymal stem cells (Ball S G et al., *Int J Biochem Cell Biol* 39:379-391, 2007). In addition, PDGFR inhibition mediated by an inhibitor regulates Oct4 and Nanog expression and changes cell morphology as well as the potency of the mesenchymal stem cells (Ball S G et al., *Stem Cells* 30:548-560, 2012). VEGF is involved in signal transduction in the mesenchymal stem cells through PDGFR (Ball S G et al., *J Cell Biol* 177:489-500, 2007), and PDGF induces proliferation and migration of ASCs through INK, and PDGF-B increases the proliferation and migration of ASCs through ROS generation and miR-210 increase (Kang et al., *J Cell Biochem* 95:1135-1145, 2005; Kim et al., *Cell Death Dis* 4:e588, 2013). PDGF secreted from ASCs induces the anagen of a hair cycle due to such a paracrine effect (Festa et al., *Cell* 146:761-771, 2011). ASCs present in an adipose tissue secrete PDGF-D and induce epithelial-mesenchymal transition (EMT) in breast cancer (Devarajan et al., *Int J Cancer* 131:1023-1031, 2012). Isoforms of PDGFs and their receptors serve as autocrines and paracrines in ASCs, but the mechanism for ASC regulation has not been fully identified.

The mitogenic effect of PDGF-B in ASCs has been known, and it is also known that PDGF-B is involved in the expression of growth factors such as PDGF-A, PDGF-B, VEGF, EGF, IGF and bFGF, and thus has a large influence on the proliferation and migration of ASCs (Kim et al., *Cell Death Dis* 4:e588, 2013; Kaewsuwan et al., *Expert Opin Biol Ther* 12:1575-1588, 2012). However, ASCs are exogenous since ASCs do not express PDGF-B. Also, it was confirmed that inhibition of PDGFR-β reduces the proliferation and migration of ASCs (Kim et al., *Cell Death Dis* 4:e588, 2013), and except PDGF-B, PDGF-A, -C and -D are expressed in ASCs (Devarajan et al., *Int J Cancer* 131:1023-1031, 2012). It has been shown that PDGF-D serves as a cell transformation factor and an angiogenetic growth factor through PDGFR-β in cancer cells (Li et al., *Oncogene* 22:1501-1510, 2003) and more effectively increases migration and invasion than PDGF-B (Najy et al., *Mol Cancer Res* 10:1087-1097, 2012). However, the function of PDGF-D in ASCs, particularly its effect on secretion of growth factors, has not been identified yet.

SUMMARY

An aspect of the present invention is directed to providing a method for proliferating stem cells, which includes culturing stem cells in PDGF-D-containing media.

An aspect of the present invention is also directed to providing a composition for promoting proliferation or migration of stem cells, which comprises PDGF-D as an active ingredient.

An aspect of the present invention is also directed to providing a medical and pharmaceutical composition for promoting hair growth or a cosmetic for preventing or reducing hair loss, which comprises PDGF-D-treated stem cells or a culture medium thereof.

An aspect of the present invention is also directed to providing a method for promoting hair growth, which includes administrating a composition comprising PDGF-D-treated stem cells or a culture medium thereof as an active ingredient into a subject.

One aspect of the present invention provides a method for proliferating stem cells, which includes culturing stem cells in a PDGF-D added medium.

Another aspect of the present invention provides a composition for promoting proliferation or migration of stem cells, which comprises PDGF-D as an active ingredient.

Still another aspect of the present invention provides a medical and pharmaceutical composition for promoting hair growth, which comprises PDGF-D-treated stem cells or a culture medium thereof as an active ingredient.

Yet another aspect of the present invention provides a method for promoting hair growth, which comprises administrating a composition comprising PDGF-D-treated stem cells or a culture medium thereof as an active ingredient into a subject.

A further aspect of the present invention provides a cosmetic for preventing or reducing hair loss, which comprises PDGF-D-treated stem cells or a culture medium thereof as an active ingredient.

PDGF-D-treated ASCs according to embodiments of the present invention increases generation of ROS in mitochondria, and proliferation and migration are increased by stimulating ASCs by the ROS. This is related not only to activation of the PI3K/Akt pathway but also to promotion of phosphorylation of p66Shc protein of a PDGF receptor.

BRIEF DESCRIPTION OF THE DRAWINGS

The above and other features and advantages of the present invention will become more apparent to those of ordinary skill in the art by describing in detail embodiments thereof with reference to the accompanying drawings, in which:

FIG. 1B: cell numbers against treatment of PDGF isoforms; FIG. 1C: cell migration against treatment of PDGF isoforms; FIG. 1D: ASC proliferation rates against treatment of PDGF isoforms; FIG. 1E: cell numbers against PDGF-D treatment; FIG. 1F: cell migration against PDGF-D treatment);

FIG. 2B: cell numbers against treatment of Akt and ERK inhibitors; FIG. 2C: cell migration against treatment of Akt and ERK inhibitors);

FIG. 3B: treatment of PDGFR inhibitor; FIG. 3C: treatment of mitochondrial ROS scavenger; FIG. 3D: measurement of mitochondrial ROS using Mito-Sox; FIG. 3E: cell numbers against treatment of mitochondrial ROS scavenger; FIG. 3F: cell migration against treatment of mitochondrial ROS scavenger);

FIG. 4B: cell numbers against treatment of inhibitor for mitochondrial fission; FIG. 4C: cell migration against treatment of inhibitor for mitochondrial fission);

FIG. 5B: intracellular p66Shc against PDGF-D treatment; FIG. 5C: inhibition of mitochondrial fission against p66Shc siRNA treatment; FIG. 5D: cell numbers against p66Shc siRNA treatment; FIG. 5E: cell migration against p66Shc siRNA treatment);

FIGS. 6B, 6D: qPCR; FIGS. 6E, 6F: treatment of PDGFR inhibitor);

FIG. 8B: hair weight measured on day 14 of hair regeneration; FIG. 8C: increase in growth factor expression analyzed by PCR array; FIG. 8D: mRNA expression of growth factors analyzed by qPCR); FIG. 9B: mRNA analysis for growth factor through qPCR after treatment of inhibitor for the MAPK pathway; FIG. 9C: diagram showing regulation of function of PDGF-D-treated ASCs).

DETAILED DESCRIPTION OF EMBODIMENTS

Unless defined otherwise, all of the technical and scientific terms used in the specification have the same meanings as conventionally understood by those of skilled in the art. Generally, the nomenclature used in the specification is well known and conventionally used in the art.

The inventors have achieved development of a material for cosmetics using an adipocyte culture medium, but it was difficult to culture enough ASCs for production for treatment. Also, there were still needs for reducing production cost.

As a result, the inventors examined novel growth factors for improving production yield of ASCs and increasing regenerative potential and found PDGF-D that had not been reported yet. As a result of attempting to identify the signaling pathways and molecular mechanisms of ASCs involved in improvement of hair regenerative potential, the inventors identified that proliferation and migration of ASCs and secretion of growth factors are increased by pretreatment of PDGF-D, confirmed improvement of the hair regenerative potential due to the increase.

Also, the inventors identified that reactive oxygen species (ROS) are generated when PDGF-D stimulates mitochondria and serve as a neurotransmitter to activate a mitogen-activated protein kinase (MAPK) pathway which is a signaling pathway related to cell growth and division to promote secretion of hair regenerative proteins.

Figure 9A:
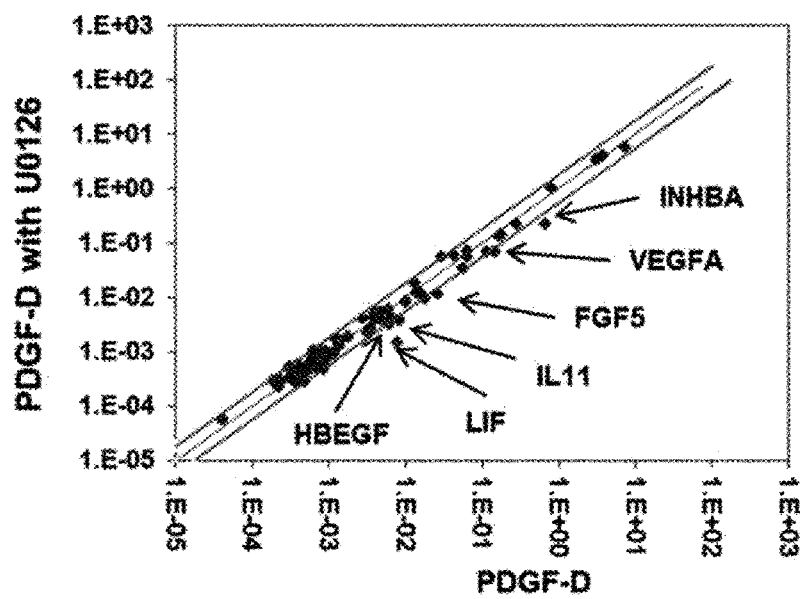
FIGS. 9A to 9C show an MAPK pathway-mediated growth factor in PDGF-D-treated ASCs (FIG. 9A: decrease in growth factor expression analyzed by PCR array after treatment of inhibitor for the MAPK pathway.
Figure 9B:
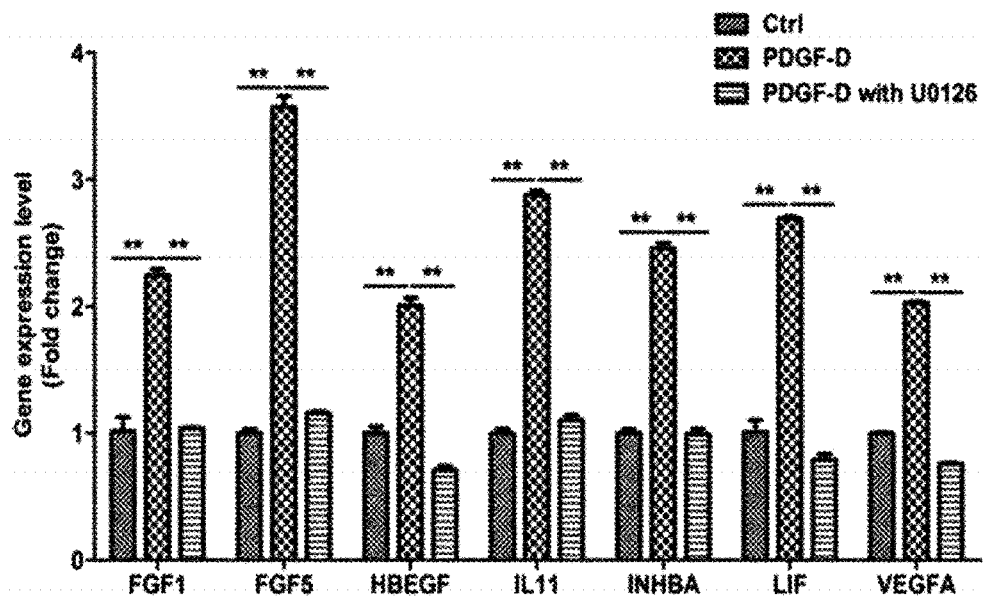
Figure 9C:
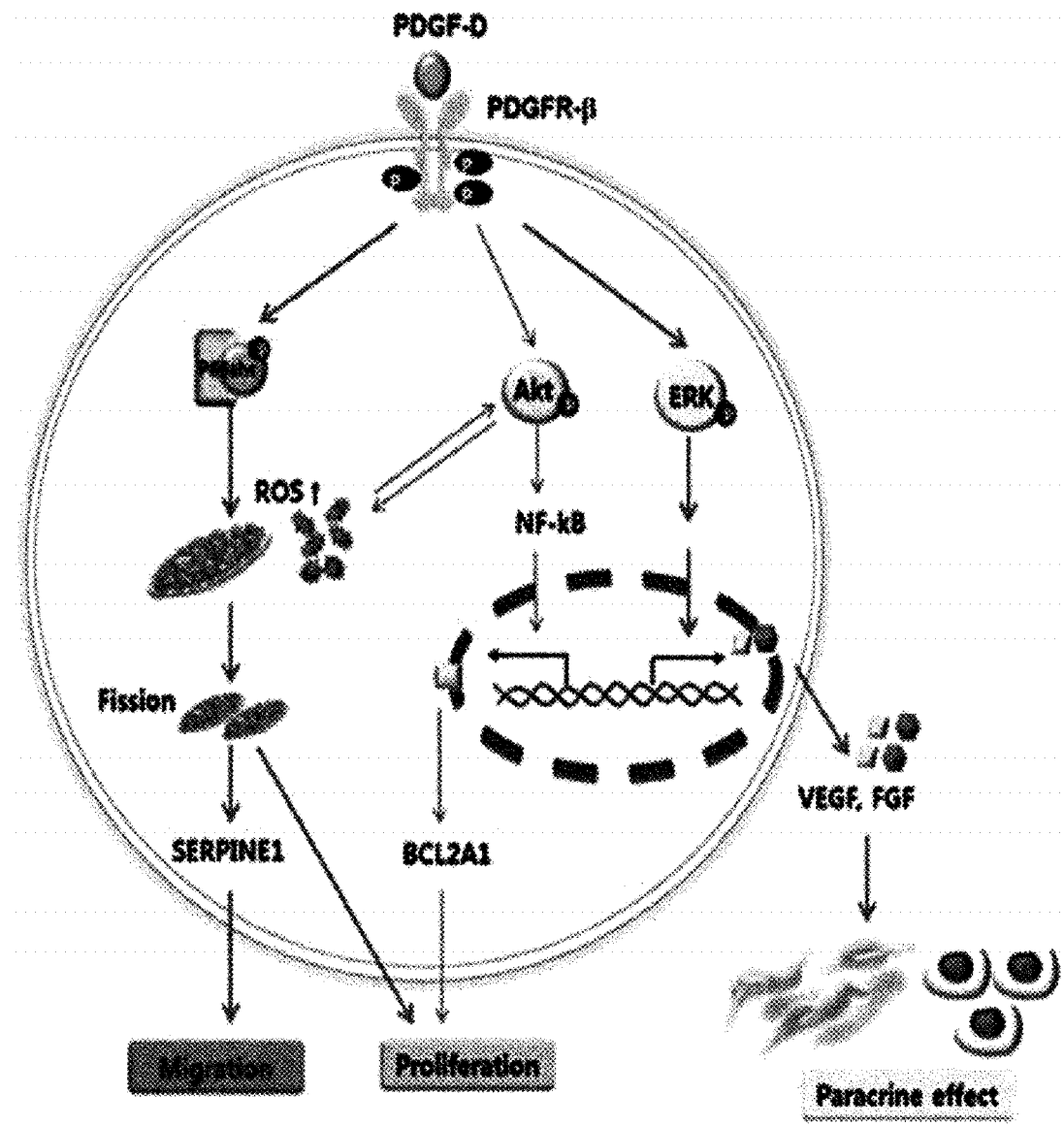

In embodiments of the present invention, the role of secreting autocrines and paracrines of PDGF-D in ASCs were investigated, and a signaling pathway involved in stimulation by PDGF-D in ASCs and a molecular mechanism were investigated (FIG. 9C). As a result, it was confirmed that PDGF-D increases migration and proliferation of ASCs due to mitochondrial ROS generation and mitochondrial fission and increases the expression of various growth factors including VEGFA, FGF1, FGF5, LIF, INHBA, IL11, HBEGF, etc. Therefore, it was learned that PDGF-D increases hair regenerative potential of ASCs.

Therefore, one aspect of the present invention relates to a method for proliferating stem cells which includes culturing stem cells in a PDGF-D added medium.

In embodiments of the present invention, the concentration of PDGF-D may be 1~50 ng/ml, but the present invention is not limited thereto.

In embodiments of the present invention, the stem cells are derived from a fat, but the present invention is not limited thereto.

The method for proliferating stem cells with increased proliferation and migration according to embodiments of the present invention may effectively overcome a problem of high cost in the development of a cellular therapeutic agent by enhancing production yield due to shortened culture time.

In embodiments of the present invention, the ASCs may have one or more characteristics of i) an increase in an Akt or ERK phosphorylation level; ii) an increase in ROS generation; iii) induction of mitochondrial fission; and iv) an increase in growth factor expression or secretion.

In embodiments of the present invention, the growth factor may be one or more selected from the group consisting of vascular endothelial growth factor A (VEGFA), fibroblast growth factor 1 (FGF1), fibroblast growth factor 5 (FGF5), bone morphogenetic protein 8B (BMP8B), leukocyte migration inhibitory factor (LIF), inhibin beta A (INHBA), interleukin 11 (IL11) and heparin-binding EGF-like growth factor (HBEGF).

In embodiments of the present invention, the "growth factor" is a protein involved in growth and differentiation of cells, which is necessary for a normal cell cycle and plays an important role for maintaining and repairing tissues.

The term "PDGF-D" used herein is one of the growth factors inducing the proliferation and differentiation of cells, and a protein for promoting the proliferation of mesenchymal cells such as smooth muscle cells, fibroblasts and blood vessel walls. In embodiments, when PDGF-D stimulates mitochondria, ROS is generated, serves as a signal transduction substance to activate an MAPK signaling pathway related to cell growth and division, and promote secretion of a hair regenerative protein.

The term "MAPK pathway" used herein is one of the signal transducers for delivering signals for growth received from a receptor on a cell membrane to a cell nucleus and serves to promote the expression of a gene related to cell proliferation and migration.

In another aspect of the present invention relates to a composition for promoting the proliferation or migration of stem cells, which comprises PDGF-D as an active ingredient.

In embodiments of the present invention, the composition may comprise an α-MEM medium, but the present invention is not limited thereto.

In embodiments of the present invention, the stem cells may be derived from a fat, but the present invention is not limited thereto.

Still another aspect of the present invention relates to a medical and pharmaceutical composition for promoting hair growth, which comprises PDGF-D-treated stem cells or a culture medium thereof as an active ingredient.

In embodiments of the present invention, the composition may further comprise a pharmaceutically acceptable carrier. Pharmaceutically acceptable carriers and preparations are described in detail in Remington's Pharmaceutical Sciences (19th ed., 1995).

In embodiments of the present invention, when the medical and pharmaceutical composition is parenterally administered, intravenous injection, subcutaneous injection, intramuscular injection, abdominal injection, percutaneous injection, etc. may be used, and an administration route may be determined depending on a type of applicable disease. For example, the medical and pharmaceutical composition of embodiments of the present invention is used to prevent and treat promotion of hair growth or hair loss and therefore may be administered by topical application. Therefore, the medical and pharmaceutical composition for promoting hair growth of embodiments of the present invention may be an injective solution for topical administration, but the present invention is not limited thereto.

In addition, a suitable dose of the medical and pharmaceutical composition or therapeutic agent of embodiments of the present invention varies according to parameters such as a preparation method, an administration method, a patient's age, body weight and sex, a pathological state, the duration of administration, an administration route and reaction sensitivity, and an ordinarily skilled doctor may facilitate the determination and prescription of an effective dose for desired treatment. The PDGF-D-pretreated ASCs of embodiments of the present invention may obtain an effect of promoting hair growth even with a small amount of cells in cellular therapy, and thus the dose of ASCs can be reduced in the cellular therapy.

As a pharmaceutically acceptable carrier used in the composition of embodiments of the present invention prepared in a liquid solution, a saline solution, a sterilized solution, a Ringer's solution, buffered saline, an albumin injective solution, a dextrose solution, a maltodextrin solution, glycerol, ethanol, and a mixture thereof which are suitable for sterilization and a living body may be used, and when needed, another conventional additive such as an antioxidant, a buffer solution, a bacteristat, etc. may be added. Also, the carrier may be prepared in an injective form such as an aqueous solution, a suspension, an emulsion, etc. by additionally adding a diluent, a dispersant, a surfactant, a binder and a lubricant.

Also, the composition of embodiments of the present invention may be prepared for external use. As an external preparation for skin having effects of preventing hair loss, promoting hair growth and improving scalp, a salve, a cream, a gel, a liquid, an emulsion, a patch or a spray may be used, but the present invention is not limited thereto.

Yet another aspect of the present invention relates to a method for promoting hair growth, which includes administrating a composition comprising PDGF-D-treated stem cells or a culture medium thereof as an active ingredient into a subject.

In embodiments of the present invention, the subject may include one or more selected from the group consisting of a chicken, a duck, a dog, a pig, a cow, a horse and a human, but the present invention is not limited thereto, and the subject may have hair loss or alopecia.

The "hair loss" or "alopecia" used herein may include alopecia areata, androgenetic alopecia, telogen effluvium, trichotilomania, anagen effluvium such as pressure alopecia, tinea capitis, alopecia syphlltiac, alopecia seborrhecia, symptomatic alopecia, non-cicatrical alopecia, cicatrical alopecia, congenital alopecia, etc. according to a type, symptom or cause, but the present invention is not limited thereto.

A further aspect of the present invention relates to a cosmetic for preventing or reducing hair loss, which comprises PDGF-D-treated stem cells or a culture medium thereof.

In embodiments of the present invention, the cosmetic may be prepared in any form conventionally prepared in the art, for example, a hair tonic, a hair conditioner, a hair essence, a hair lotion, a hair nutrient lotion, a hair shampoo, a hair rinse, a hair treatment, a hair cream, a hair nutrient cream, a hair moisturizing cream, a hair massage cream, a hair wax, a hair aerosol, a hair pack, a hair nutrient pack, a hair soap, a hair cleansing foam, a hair oil, a hair drying agent, a hair preservative, a hair coloring agent, a hair waving agent, a hair decolorant, a hair gel, a hair glaze, a hair dressinger, a hair laquer, a hair moisturizer, a hair mousse or a hair spray, but the present invention is not limited thereto.

In embodiments of the present invention, the cosmetic may comprise ingredients conventionally used in a cosmetic composition, for example, conventional supplementary agents such as an antioxidant, a stabilizer, a solubilizing agent, a vitamin, a pigment and a fragrance in addition to PDGF-D-pretreated ASCs as an active ingredient.

The term "promotion of hair growth" or "prevention of hair loss" used herein includes other terms used in the art such as hair nourishing or hair development.

A part of body to which the medical and pharmaceutical composition for promoting hair growth or a cosmetic of embodiments of the present invention can be applied may be any part of the body including the scalp needing hair growth. For example, the composition or a cosmetic of embodiments of the present invention can also be used for improving a part in which hair or coat is damaged due to a scar caused by external injury, a broad or M-shaped forehead simply for beautification, and condition of eyelashes or eyebrows as well as atrichia.

In embodiments of the present invention, to compare induction of an antigen phase by administering a drug from about 7 weeks after birth, C3H/HeN telogen-to-anagen transition models were used.

The term "anagen" used herein refers to a stage of growing hair at about 90% of the repeated hair growth cycles, and the term "telogen" refers to a period in which cell division of the bulb of hair for growing hair under a hair root has stopped and paused, resulting in hair loss.

EXAMPLES

Hereinafter, examples of the present invention will be described in further detail. It will be apparent to those of ordinary skill in the art that these examples are merely provided to explain the present invention in further detail, and the scope of the present invention is not limited to the examples.

Example 1 Effects of PDGF on Proliferation and Migration of Adipose-Derived Stem Cells 1-1: Culture and Identification of Human ASCs Human ASCs were obtained from a subcutaneous fat by liposuction according to a known method (Kim et al. *J Dermatol Sci* 53:96-102, 2009). ASCs were cultured in an α-MEM medium (Hyclone, Thermo Scientific) with 10% FBS (GIBCO, Invitrogen) and 1% penicillin/streptomycin (GIBCO) at 37° C. in 5% $CO_2$, and cells at 7-9 passages were used. Positive expression of CD44, CD73, CD90, CD105, HLA-1 and PODXL and negative expression of CD34 and CD45 were examined by flow cytometry (Kim et al. *Cell Death Dis* 4:e588, 2013; Kim et al., *Cell Biol Int* 38:32-40, 2014), and multipotent differentiation potential for the cells to differentiate into adipocytes, osteocytes and cartilage cells was examined (Song et al. *Stem Cells Dev* 17:451-461, 2008).

Also, the mRNA expression of PDGF isoforms and receptors thereof were identified in ASCs.

Figure 1A:
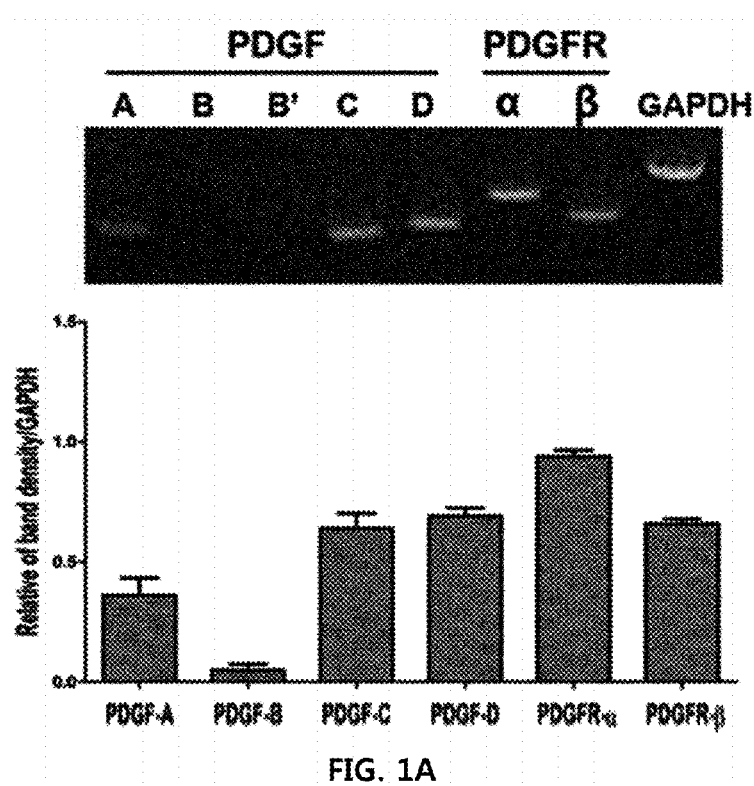
FIGS. 1A to 1F show increased proliferation and migration of ASCs by PDGF-D treatment (FIG. 1A: mRNA expression of PDGF and PDGFR isoforms.

As a result, PDGF-B was not expressed, PDGF-C and PDGF-D were highly expressed, and receptors PDGFR-α and PDGFR-β were also highly expressed (FIG. 1A).

1-2: Proliferation and Migration of ASCs

In this example, the stem cells were treated with PDGF isoforms, and cell proliferation and migration were examined. PDGF-A, -B and -C were purchased from Sigma, and PDGF-D was purchased from R&D systems.

For cell proliferation assay, $7 \times 10^3$ of ASCs were seeded on 48-well plates, 24 hours later, a medium was transferred with a 0.2% FBS-containing α-MEM medium, and the following day, cells were treated with PDGF isoforms (10 ng/ml) for 48 hours. Afterward, the medium was removed, the cells were treated with a 10% CCK-8 solution for 2 hours using a CCK-8 assay kit (Dojindo, Japan), and the absorbance was measured at 450 nm, to examine cell numbers.

Also, for cell migration assay, $2 \times 10^4$/well of ASCs were seeded on the upper portion of a trans-well membrane plate (Corning, USA). After 2 hours, PDGF isoforms (10 ng/ml) and an α-MEM medium with 0.2% FBS were introduced to the lower portion of the trans-well membrane plate to culture the PDGF isoforms for 16 to 20 hours. Afterward, cells migrated to the trans-well membrane were fixed with cold ethanol for 20 minutes, and stained with 10% crystal-violet (Sigma, USA) at room temperature for 30 minutes.

Figure 1B:
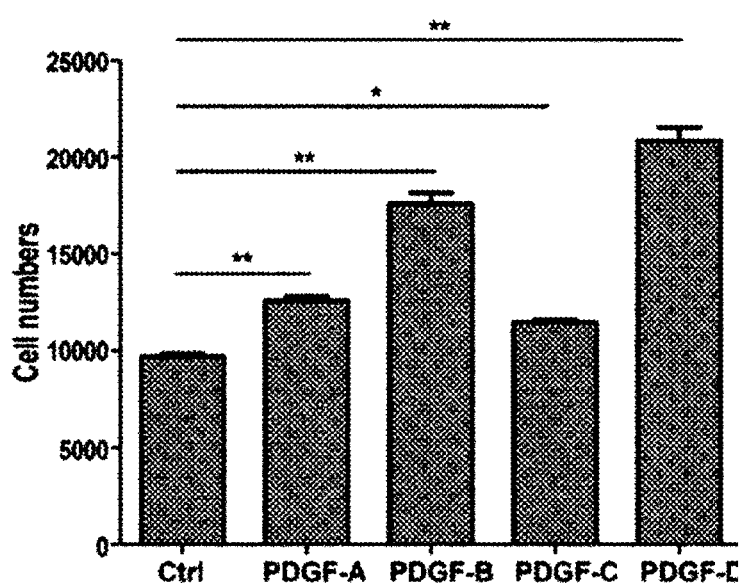
Figure 1C:
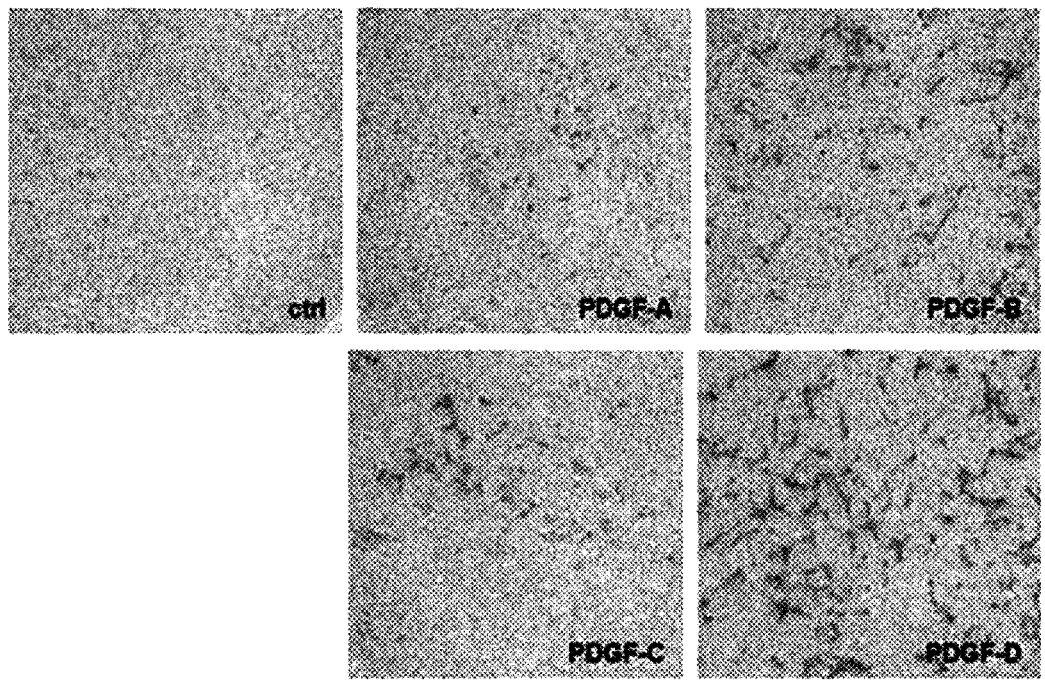
Figure 1C:
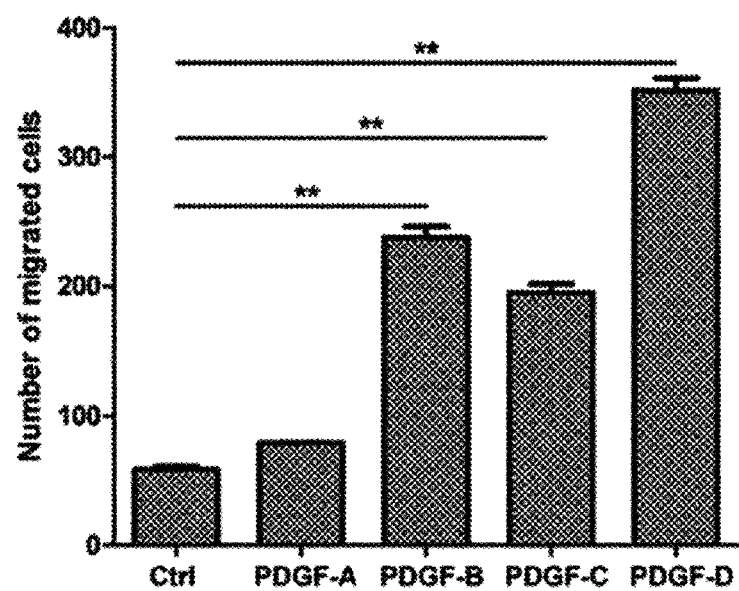

As a result, when ASCs were treated with PDGF-B and PDGF-D, cell proliferation and migration were considerably enhanced twice or more (FIGS. 1B, 1C).

In addition, the kinetics of cell proliferation was measured using an Incucyte™ live cell imaging system (Essen Bioscience, Michigan, USA). ASCs were seeded on six-well plates at a density of $1 \times 10^5$ cells per well with 0.2% FBS in a-MEM medium. The following day, cells were treated with PDGF isoforms (10 ng/ml), and ASCs were monitored with Incucyte. Cell confluence was measured at 4-h intervals for 72 hours.

Figure 1D:
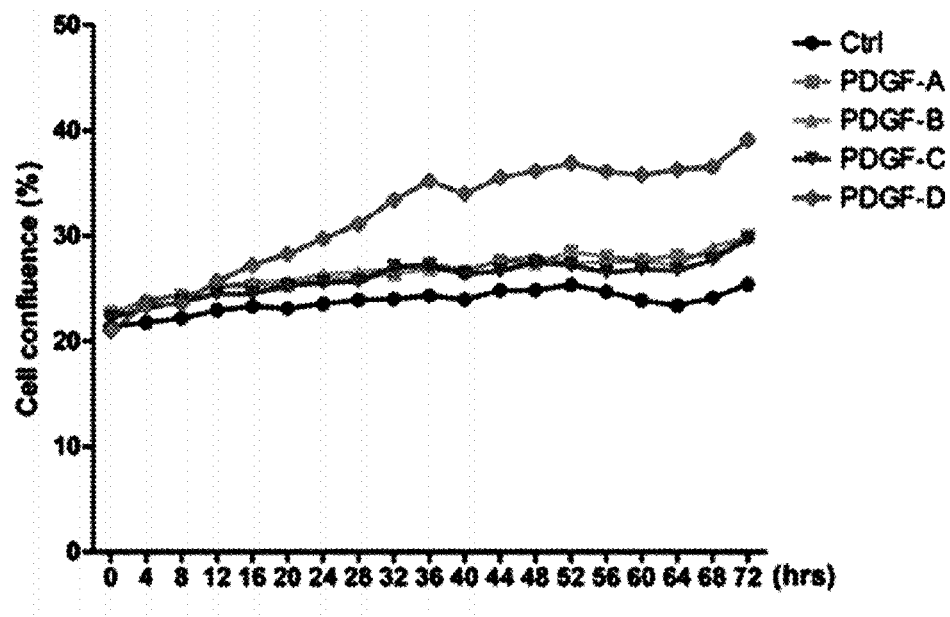

As a result, compared with other isoform proteins, PDGF-D treated cells had the highest proliferation ratio (FIG. 1D).

Also, the kinetics of cell migration was measured using scratch migration assay, which showed that PDGF-D had the most excellent migration effect.

1-3: Proliferation and Migration of ASCs by PDGF-D Treatment

Figure 1E:
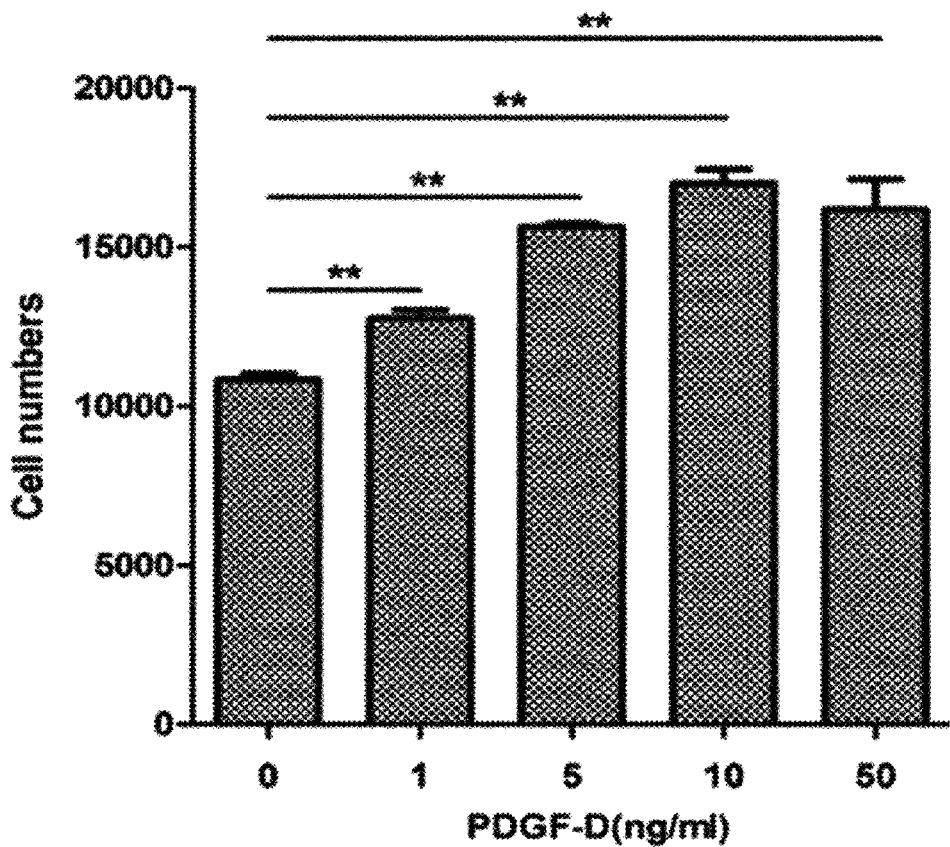
Figure 1F:
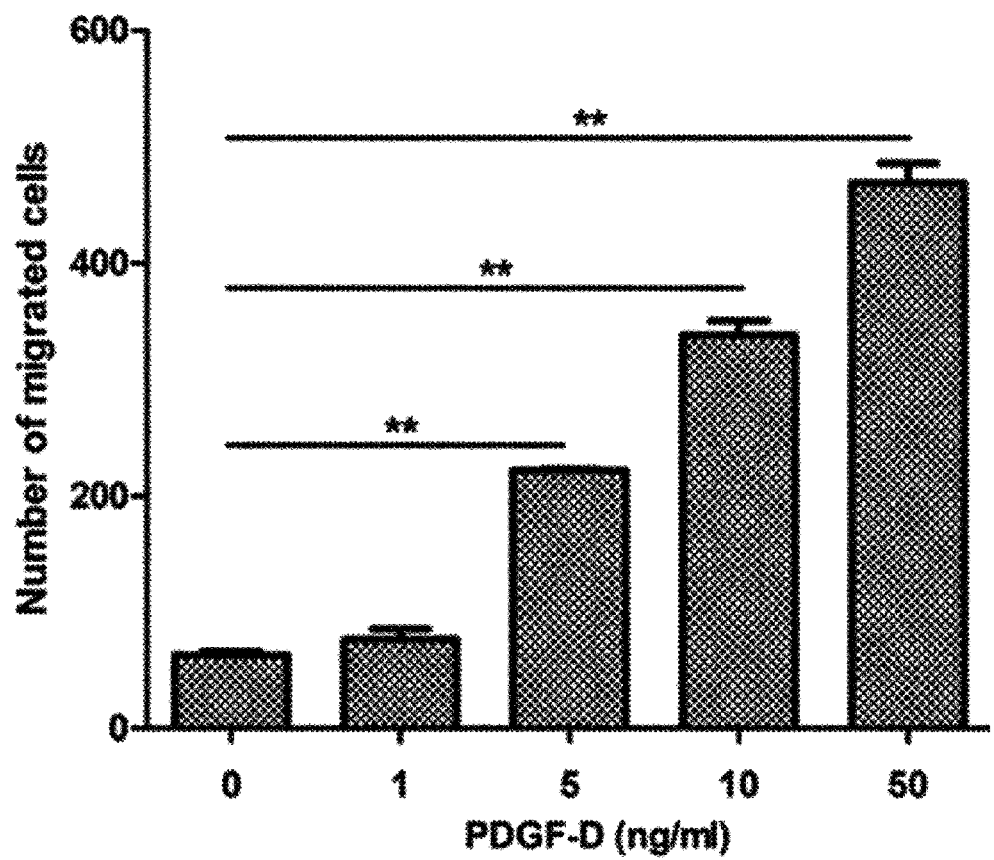

The result of analyzing proliferation and migration of PDGF-D-treated ASCs by the method described in Example 1-2 showed that the increases in proliferation and migration of ASCs were dependent on the PDGF-D concentration (FIGS. 1E, 1F).

Also, the phosphorylation of Akt and ERK in PDGF-D-treated ASCs were detected by western blotting, and cells were treated with Akt inhibitor LY294002 (Calbiochem, USA) and ERK inhibitor U0126 (Calbiochem, USA) to examine the proliferation and migration of ASCs.

Figure 2A:
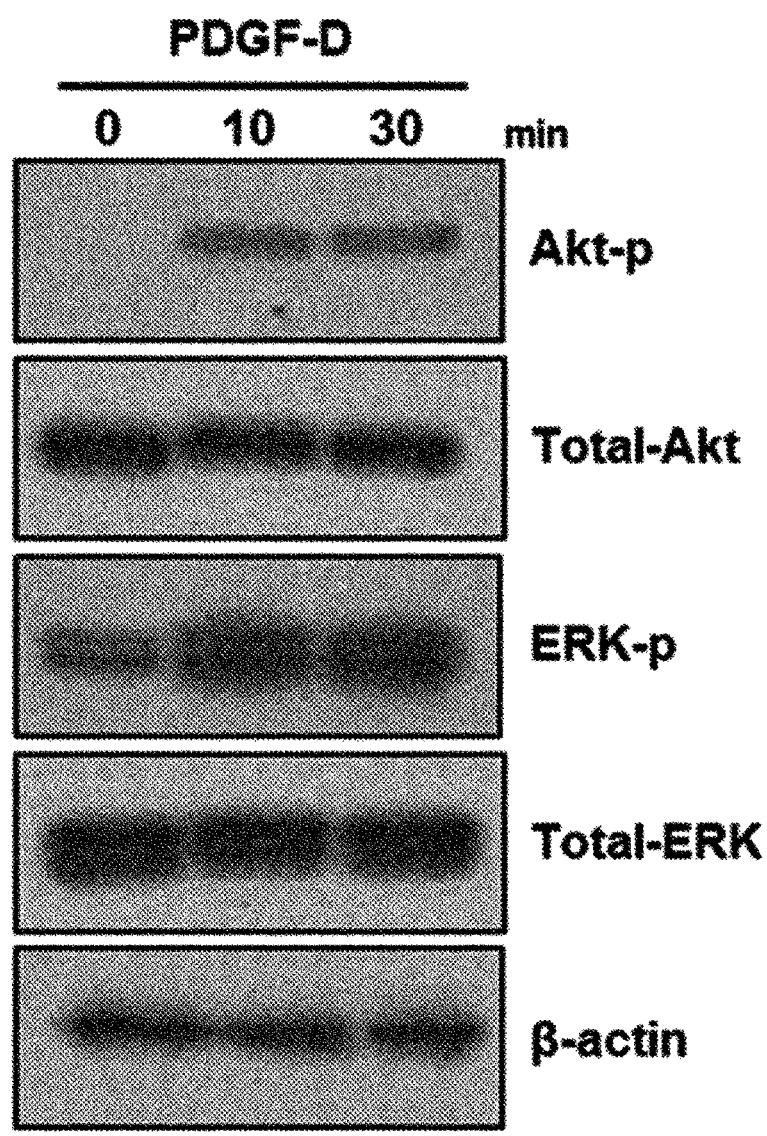
FIGS. 2A to 2C show the Akt and ERK phosphorylation of ASCs by PDGF-D treatment (FIG. 2A: phosphorylation over PDGF-D treating time.
Figure 2B:
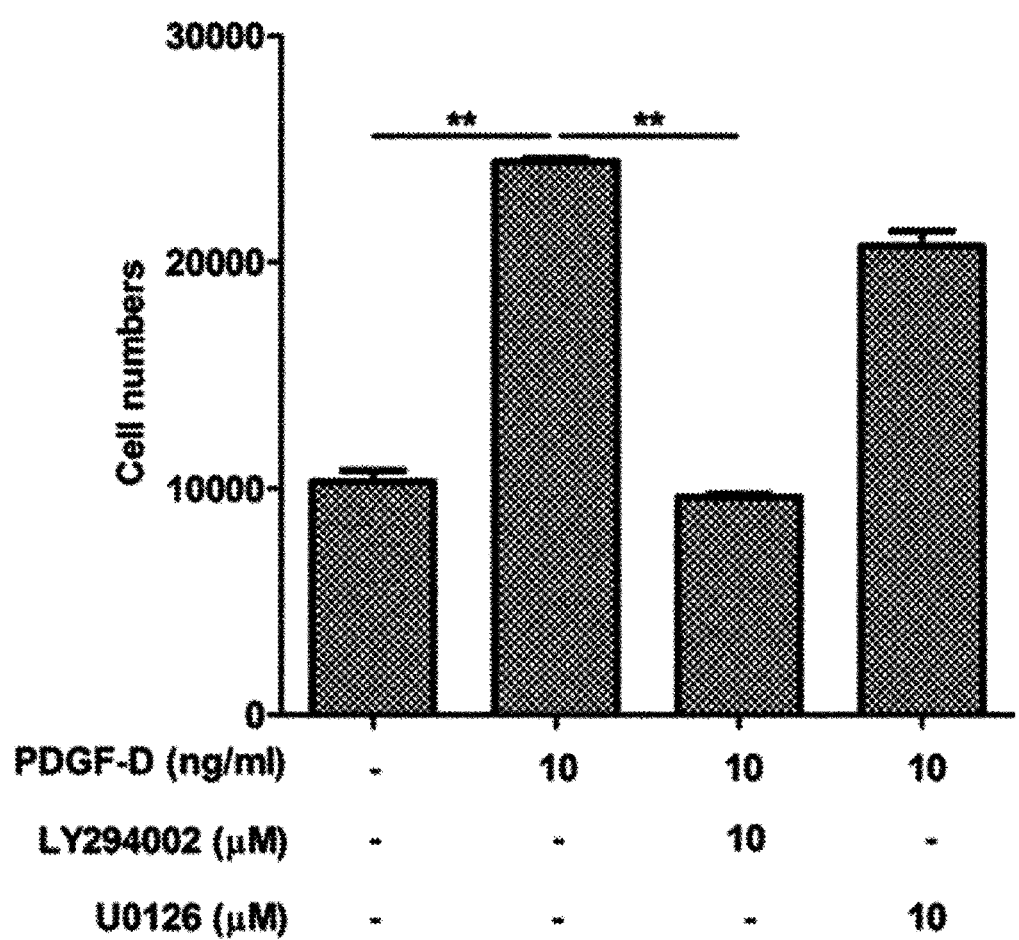
Figure 2C:
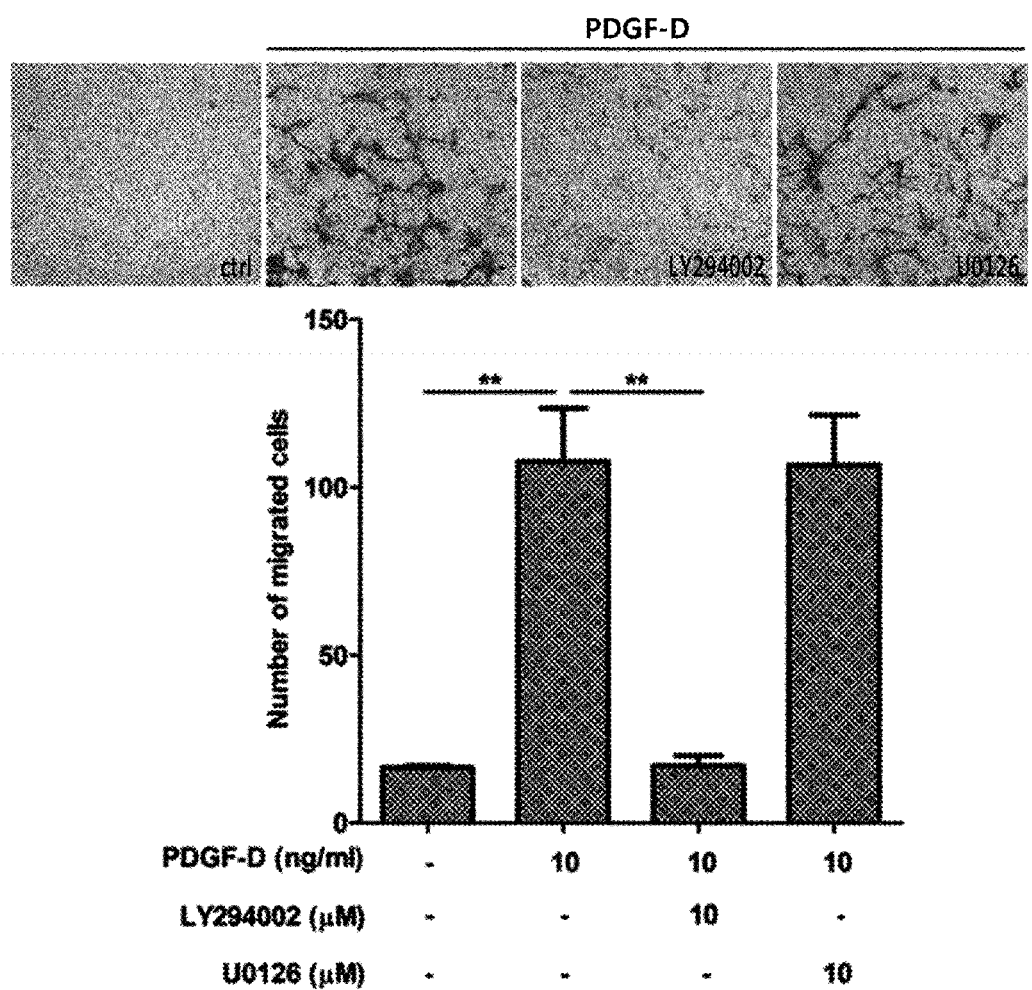

As a result, PDGF-D phosphorylated Akt and ERK of ASCs (FIG. 2A), the proliferation and migration of ASCs increased by PDGF-D were inhibited by treatment of the Akt inhibitor LY294002 (FIGS. 2B, 2C). However, the proliferation and migration of ASCs were not influenced by the treatment of the ERK inhibitor U0126.

Example 2 Generation of Mitochondrial ROS by PDGF-D Treatment

Because it has been reported that the proliferation and migration of ASCs are increased by ROS generation by PDGF-B treatment (Kim et al. *Cell Death Dis* 4:e588, 2013), in this example, ROS generation was measured after PDGF-D treatment.

ROS generation in cells were measured by a method using DCF-DA (Molecular probe, USA) (Kim et al., *Stem Cells Dev* 21:2212-2221, 2012; Kim et al., *Stem Cells Dev* 20:1753-1761, 2011), and mitochondrial ROS generation was measured using Mito-Sox (Molecular probe, USA). ASCs were seeded on 60-mm dishes, treated with PDGF-D (10 ng/ml) and 5 μM Mito-Sox and incubated in a dark place for 2 hours, and then flow cytometry was performed.

Figure 3A:
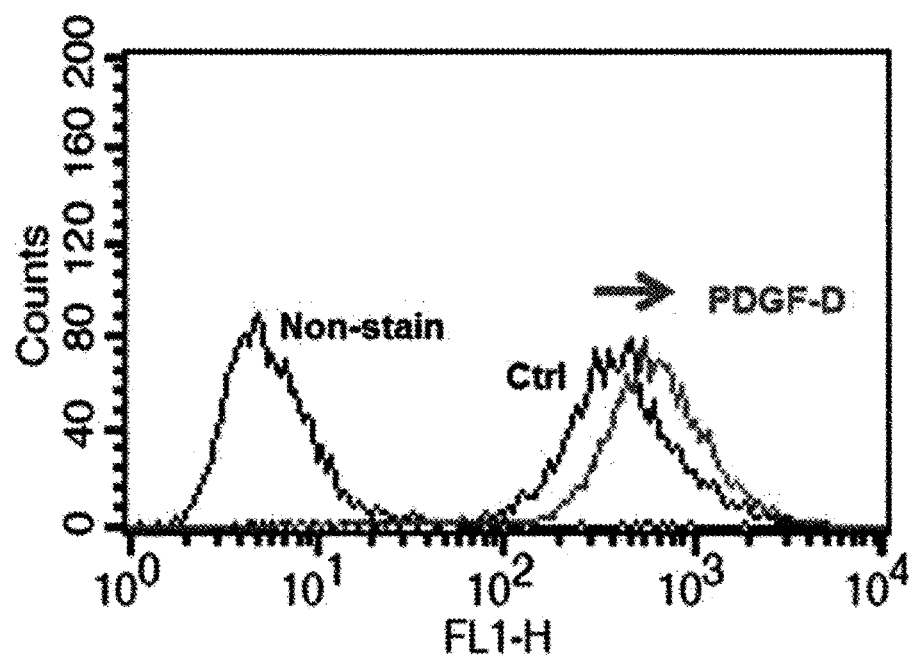
FIGS. 3A to 3F show the increase of mitochondrial reactive oxygen species (ROS) generation in ASCs by PDGF-D treatment (FIG. 3A: measurement of intracellular ROS using DCF-DA.
Figure 3B:
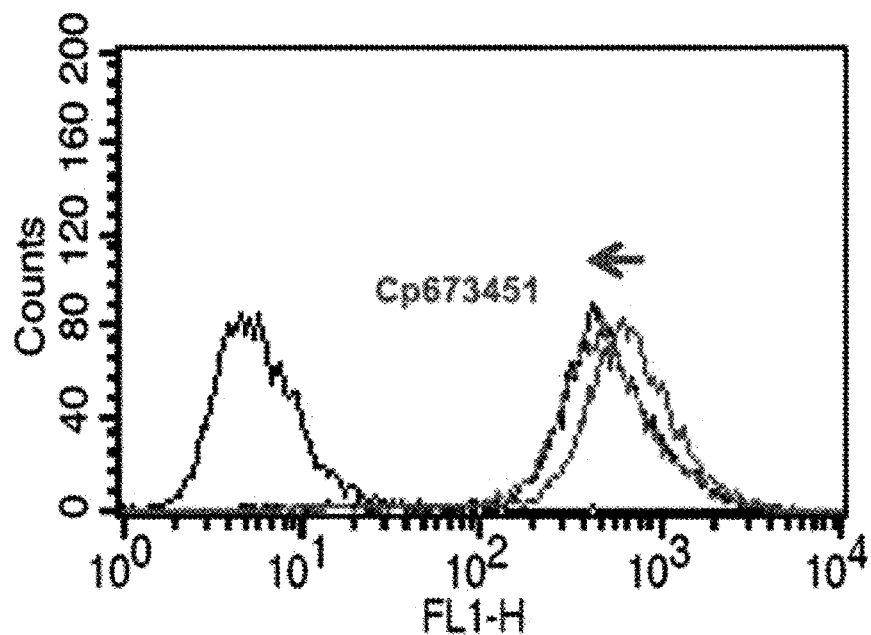
Figure 3C:
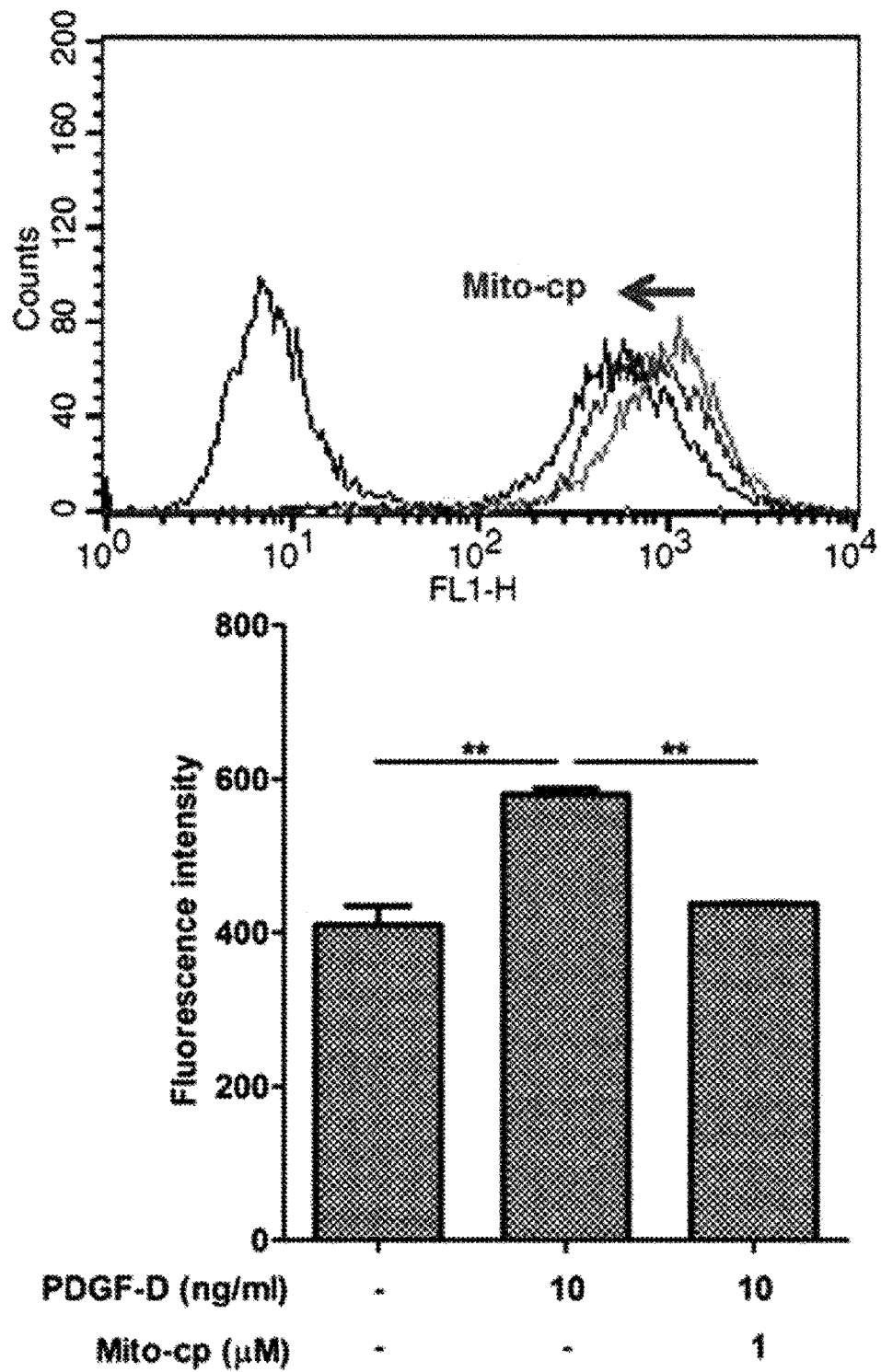

As a result, PDGF-D considerably increased DCF-DA fluorescence in ASCs (FIG. 3A), and PDGFR-β inhibitor cp673451 (Sclleckchem, USA) and mitochondrial ROS scavenger Mito-CP (Kim et al., *Cell Biol Int* 38:32-40, 2014) considerably decreased the DCF-DA fluorescence (FIGS. 3B, 3C).

Figure 3D:
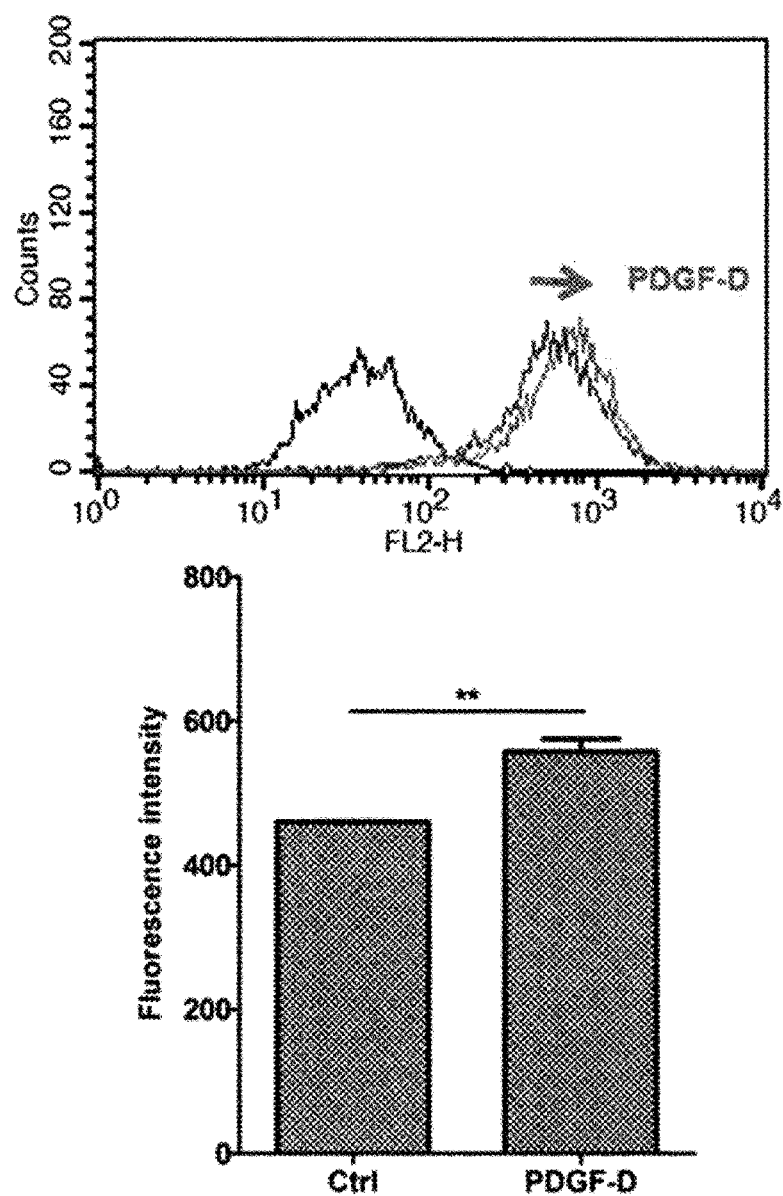
Figure 3E:
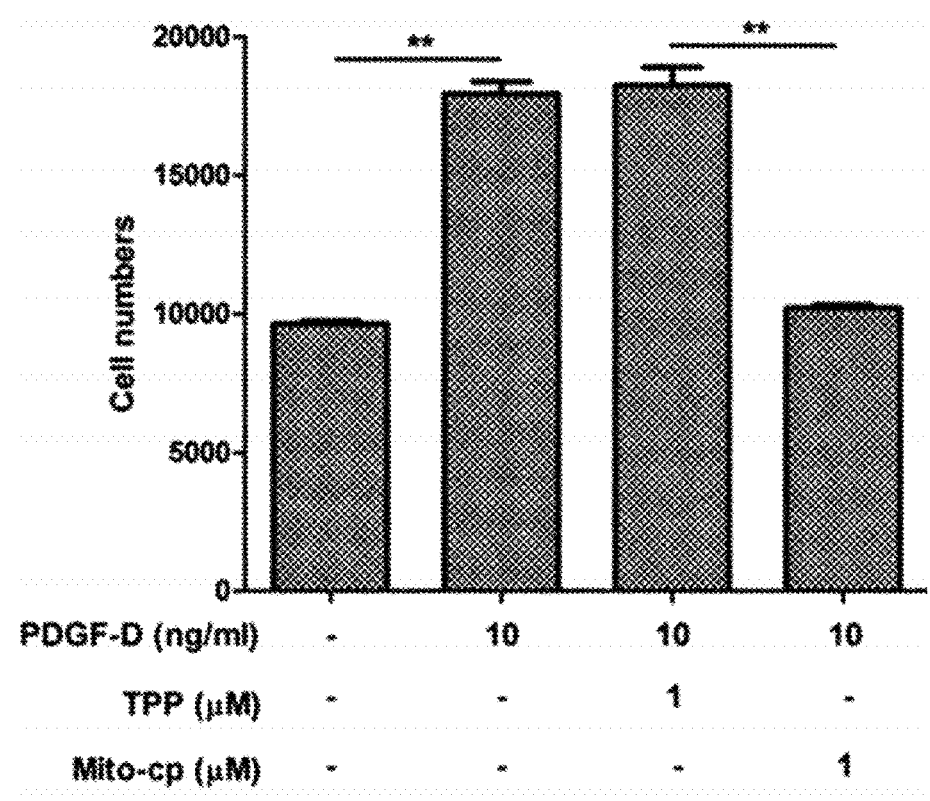
Figure 3F:
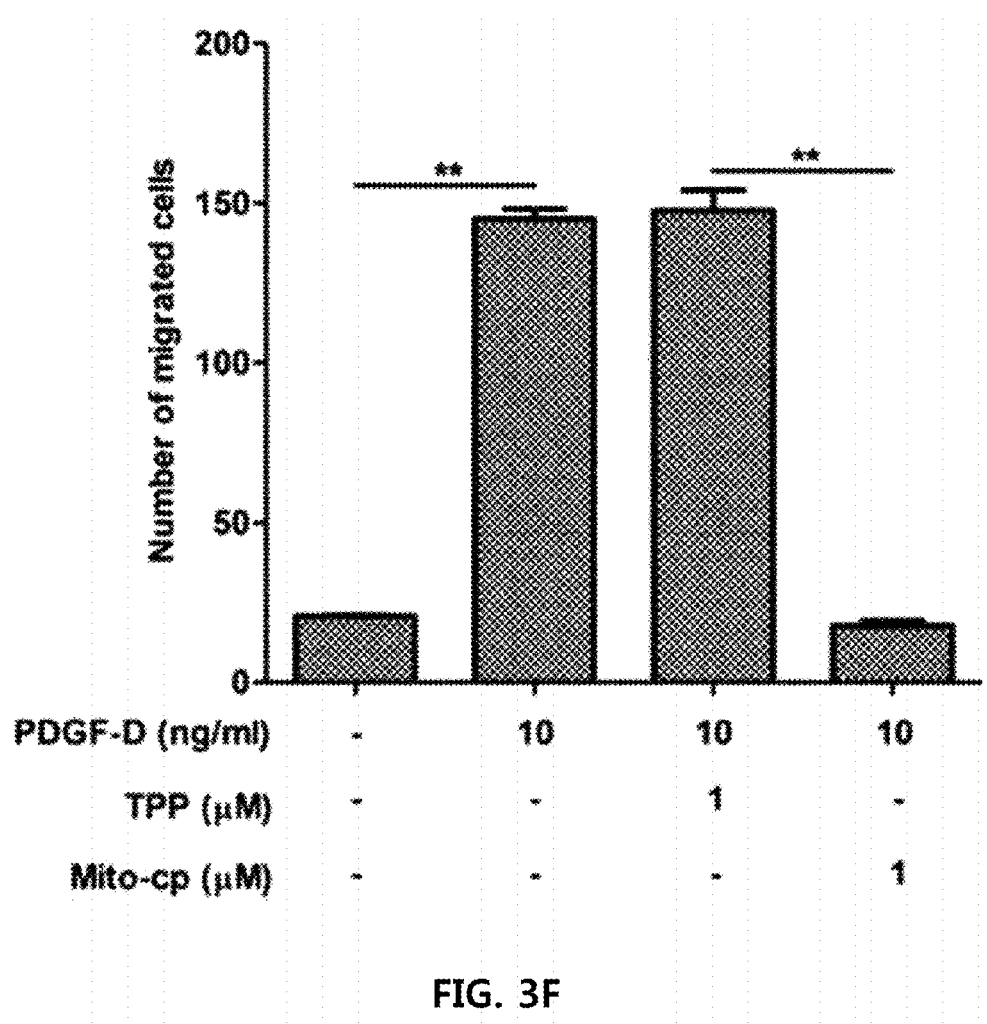

To this end, mitochondrial ROS was measured using Mito-Sox, and PDGF-D considerably increased Mito-Sox fluorescence in ASCs (FIG. 3D). Also, the mitochondrial ROS scavenger Mito-CP considerably decreased the proliferation and migration of ASCs induced by PDGF-D (FIGS. 3E, 3F). This means that PDGF-D induces the proliferation and division of ASCs by the mitochondrial ROS generation.

Example 3 Mitochondrial Fission by PDGF-D Treatment

PDGF-D increased mitochondrial ROS generation and transformed the morphology of mitochondria, and thus, in this example, mitochondrial fission after PDGF-D treatment was examined.

ASCs were seeded on a round cover glass and treated with PDGF-D (10 ng/ml) for 24 hours. For mitochondrial staining, 500 nM MitoTracker Red (Molecular Probe, USA) was added to an α-MEM medium, and cells were incubated for 30 minutes, and then the morphology of mitochondria and MitoTracker Red fluorescence were examined using a confocal microscope (Carl Zeiss). In addition, for nuclear staining, cells were fixed with 4% paraformaldehyde for 15 minutes, permeabilized with 0.5% PBS-T for 5 minutes, and stained with DAPI (Sigma, USA) at room temperature for 10 minutes.

Figure 4A:
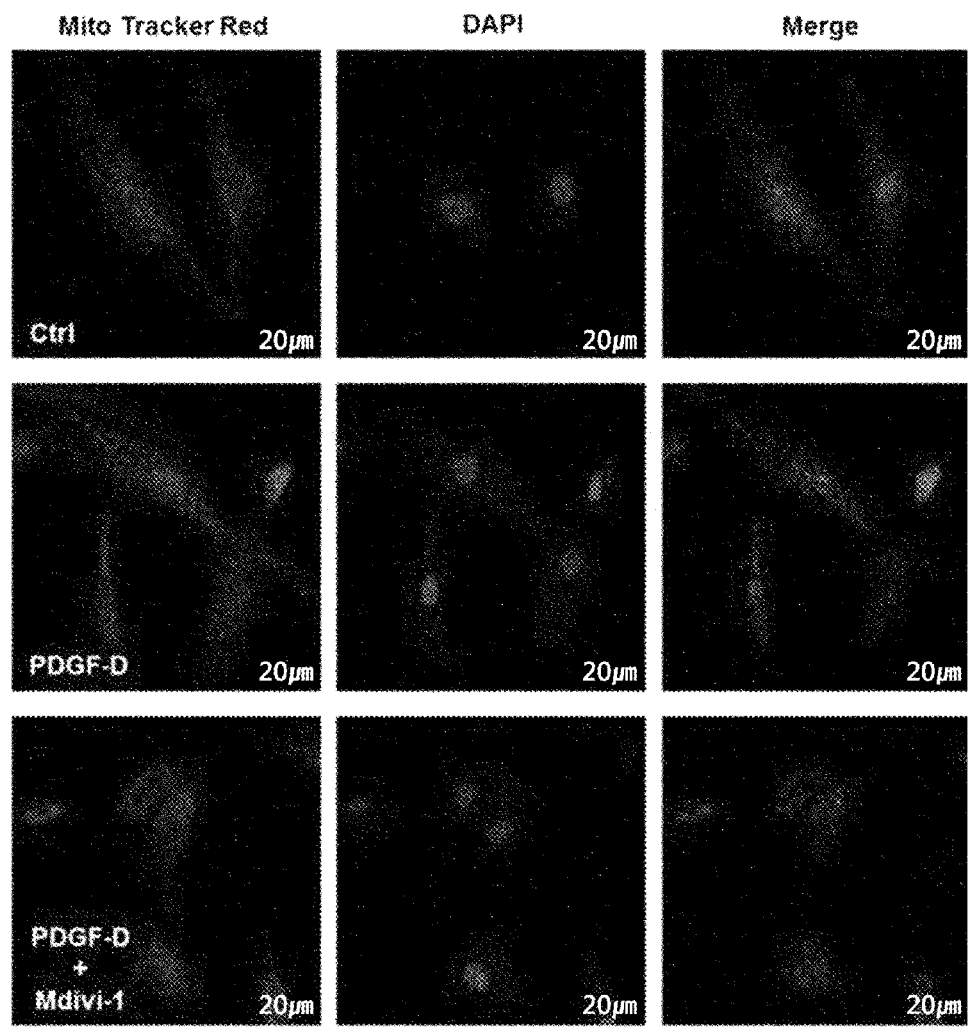
FIGS. 4A to 4C show the promotion of mitochondrial fission in ASCs by PDGF-D treatment (FIG. 4A: treatment of PDGF-D and inhibitor for mitochondrial fission.

As a result, PDGF-D considerably increased MitoTracker Red fluorescence in ASCs and increased a globularly-fragmented structure of mitochondria (FIG. 4A).

Figure 4B:
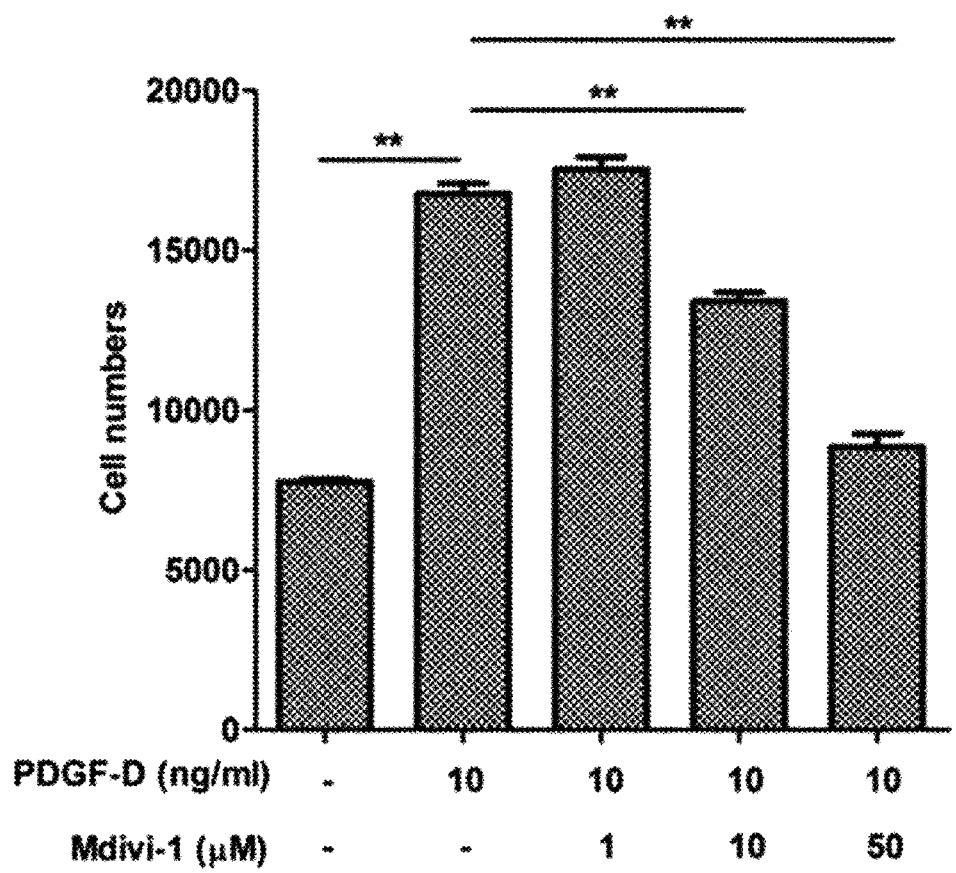
Figure 4C:
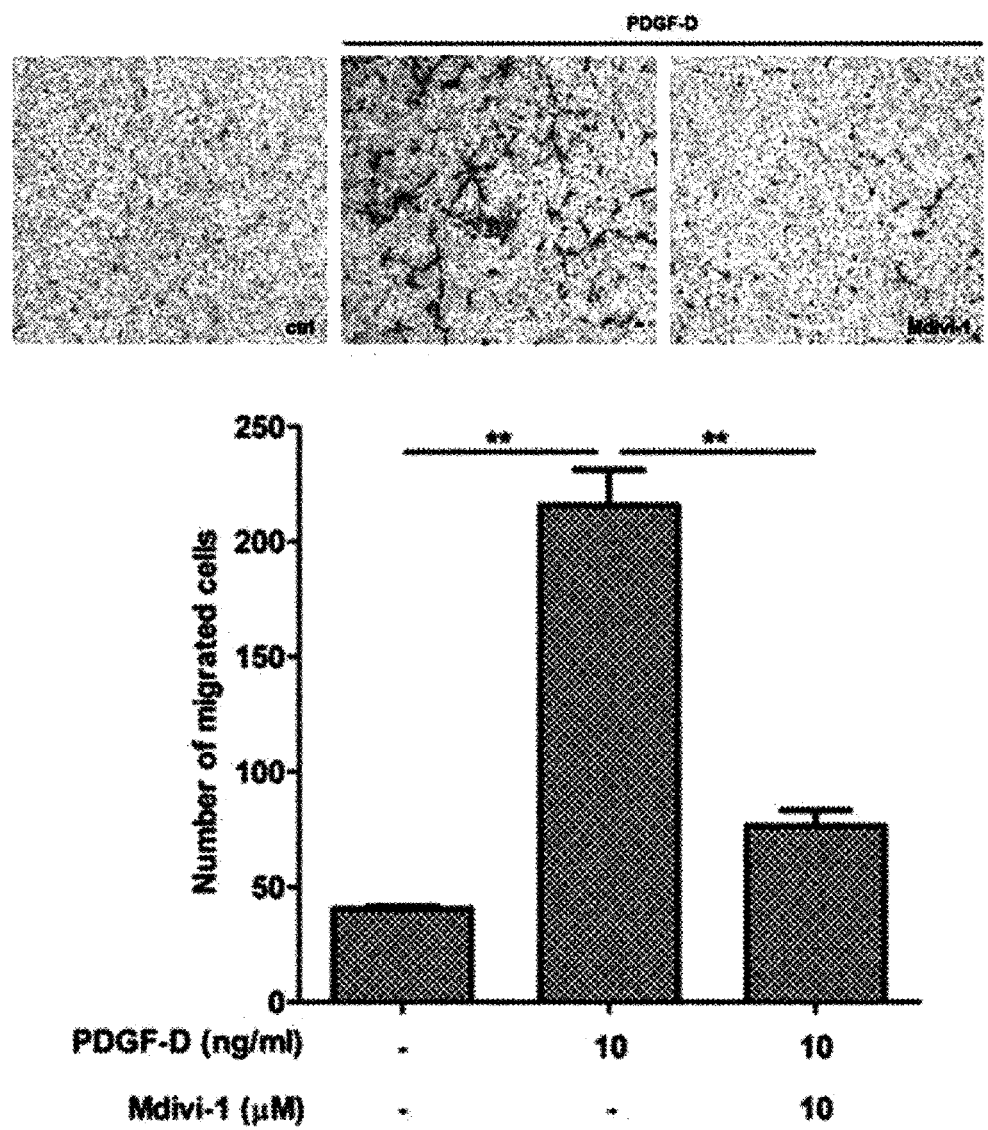

Here, a treatment with an inhibitor for mitochondrial fission Mdivi-1 (Enzo Life Science, USA) decreased the mitochondrial fission induced by PDGF-D treatment (FIG. 4A). In addition, Mdivi-1 considerably decreased ASC proliferation and migration induced by PDGF-D (FIGS. 4B, 4C). This means that PDGF-D induces the ASC proliferation and division by the mitochondrial fission.

Example 4 Phosphorylation of p66shc by PDGF-D Treatment

Recently, it has been reported that mitochondrial ROS generation is regulated by a specific enzyme such as p66shc (Migliaccio et al., *Nature* 402:309-313, 1999; Nemoto et al., *Science* 295:2450-2452, 2002), and in this example, a p66shc role in the mitochondrial fission in ASCs was investigated.

Phosphorylation of p66shc in ASCs was examined by western blotting and fluorescence staining. For p66shc-ser34 fluorescence staining, ASCs were seeded on a round cover glass, and the following day, PDGF-D (10 ng/ml) was treated for 30 minutes. Afterward, cells were fixed with 4% paraformaldehyde for 15 minutes, permeabilized with 0.5% PBS-T for 5 minutes, washed with 0.1% PBS-T, and treated with a blocking solution (10% FBS and 0.5% gelatin-added PBS) for 30 minutes. A primary antibody (p66shc-ser34; Calbiochem, USA) and a secondary antibody (FITC) were reacted, and for nuclear staining, cells were treated with DAPI and examined using a fluorescence confocal microscope.

Figure 5A:
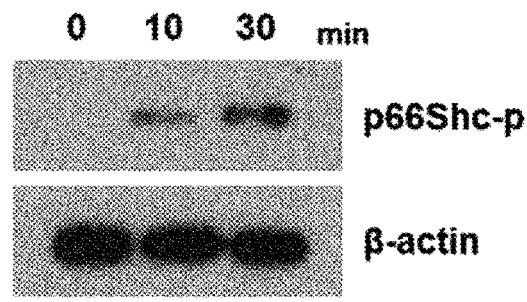
FIGS. 5A to 5E show p66Shc phosphorylation in ASCs by PDGF-D treatment (FIG. 5A: p66Shc phosphorylation over PDGF-D treating time.
Figure 5B:
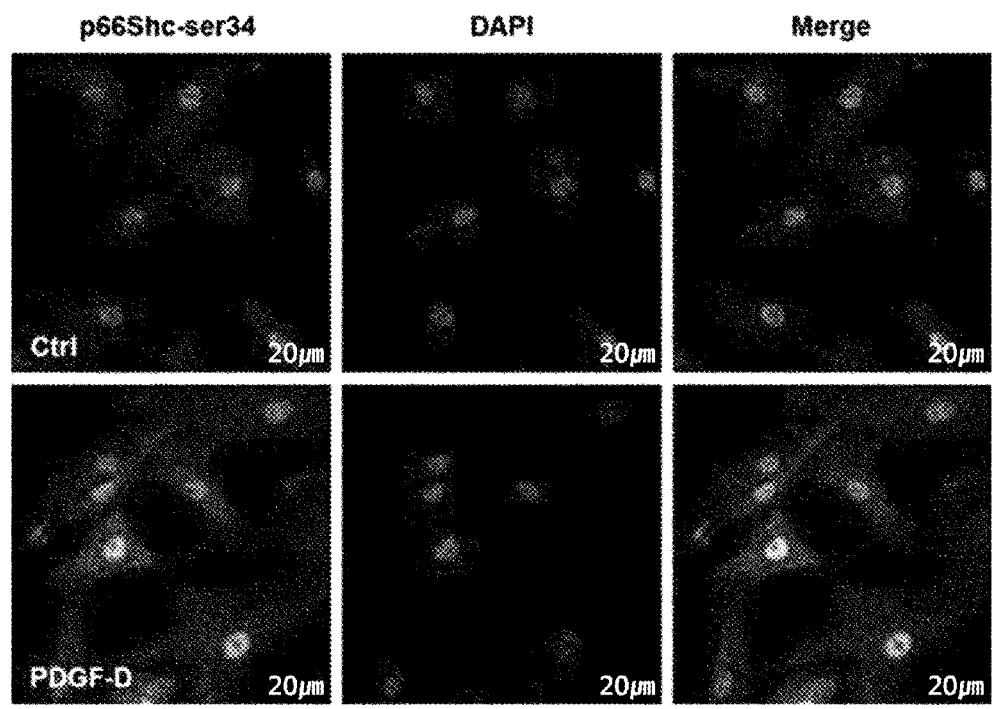
Figure 5C:
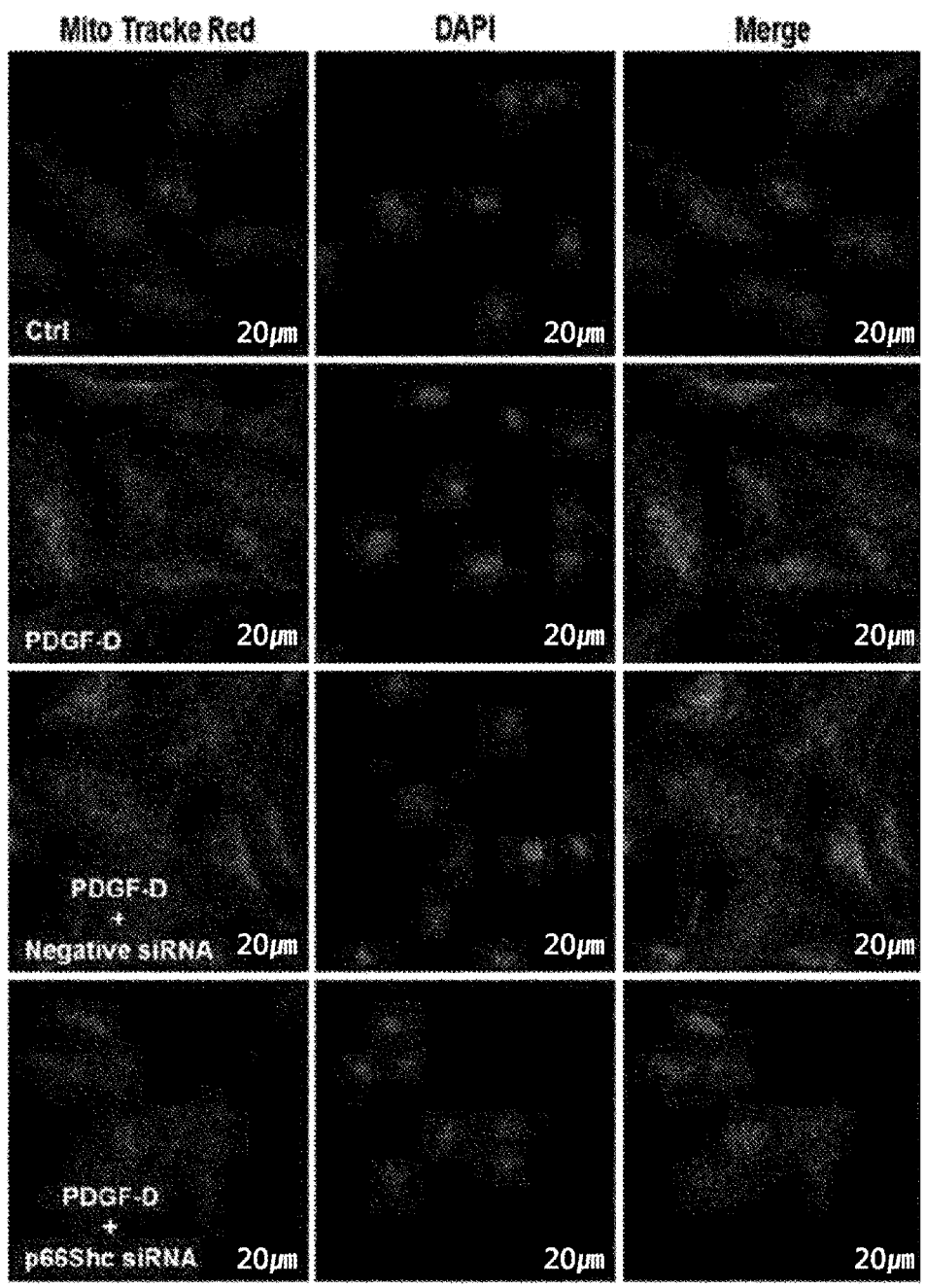
Figure 5D:
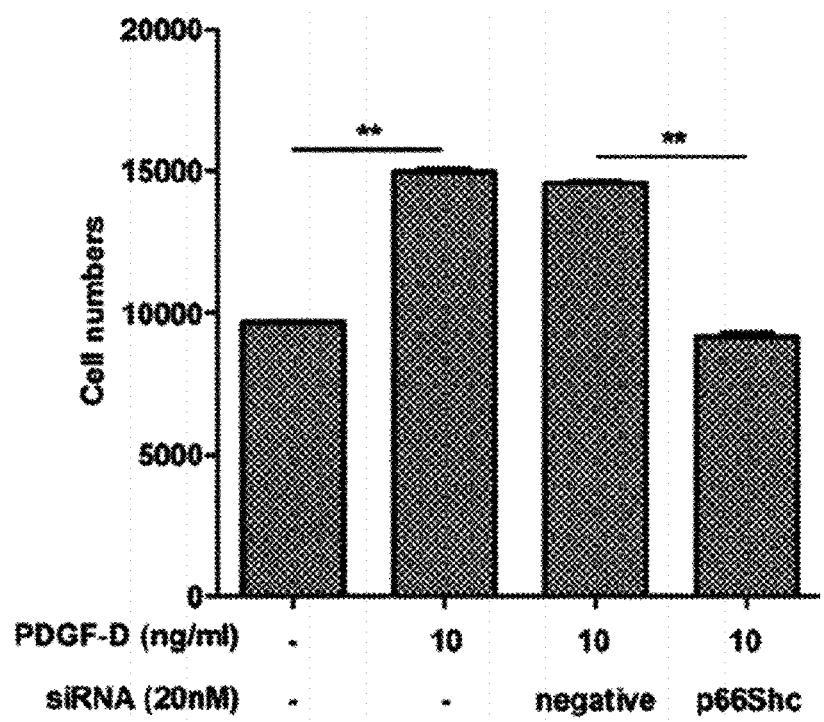
Figure 5E:
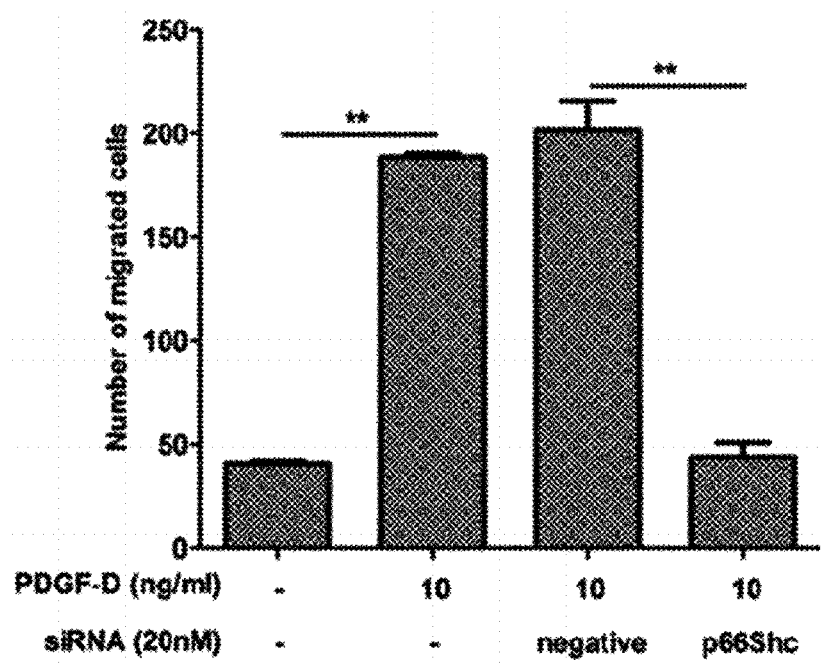

As a result, the p66shc phosphorylation in ASCs was increased by the PDGF-D treatment (FIGS. 5A, 5B). Therefore, it was confirmed that 20 nM p66shc siRNA (Dharmacon, USA) of ASCs was transfected, resulting in inhibition of the mitochondrial fission induced by the PDGF-D treatment (FIG. 5C). In addition, p66shc siRNA considerably decreased the ASC proliferation and migration induced by PDGF-D (FIGS. 5D, 5E). This means that the mitochondrial fission of ASCs was mediated by p66shc.

Example 5 Increase of BCL2A1 and SERPINE1 by PDGF-D Treatment

In this example, PDGF-D target genes were examined using a human signaling pathwayfinder $RT^2$ profiler PCR array (signaling pathway: PAHS-041ZD).

$2.5 \times 10^5$ of ASCs were seeded on 60-mm dishes, cultured in a 0.2% FBS-containing α-MEM medium, and treated with PDGF-D for 4-24 hours. Afterward, total RNA was extracted using an RNA extraction kit (RNeasy, Qiagen), cDNA was synthesized from 500 ng of total RNA by a cDNA synthesis kit (A3500, Promega) using 1,000 U reverse transcriptase and 50 ng/μl oligo(dT) primers. Gene expression was detected by a PCR array kit (Qiagen) according to the manufacturer's instructions, and qPCR was performed on a step one plus real-time PCR system (Applied Biosystems, Invitrogen) using a SYBR Green PCR master mix (Takara Bio, Japan).

Figure 6A:
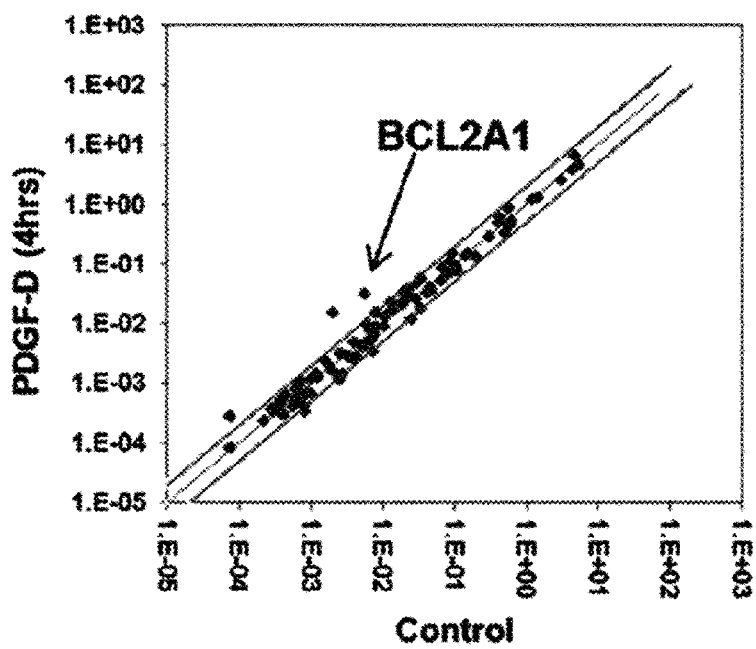
FIGS. 6A to 6F show the increase of BCL2A1 and SERPINE1 expression in ASCs by PDGF-D treatment (FIGS. 6A, 6C: PCR array.
Figure 6B:
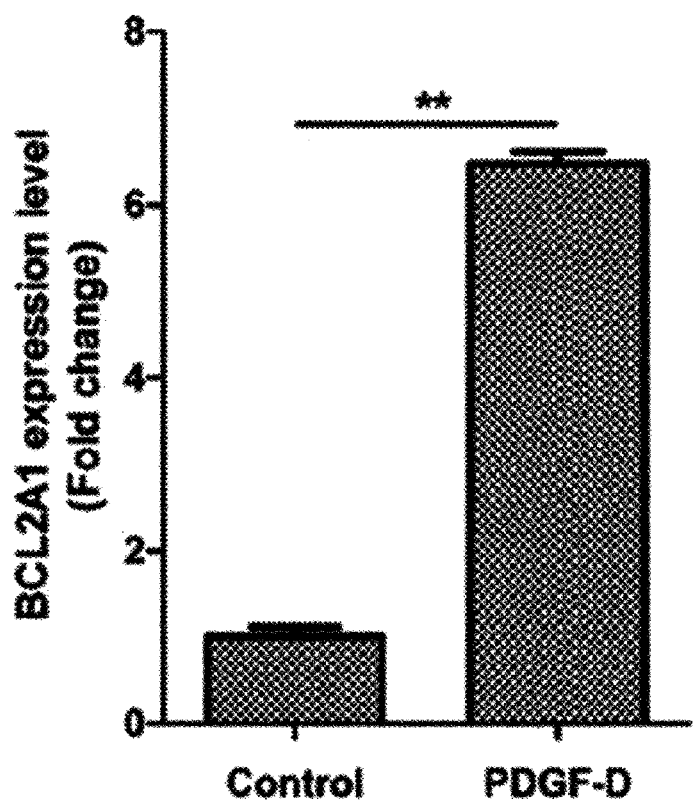
Figure 6C:
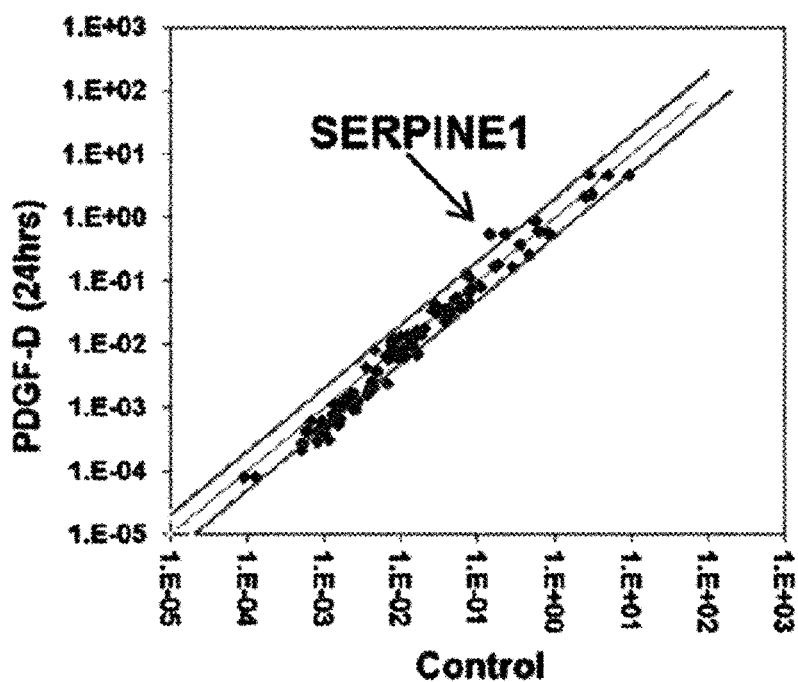
Figure 6D:
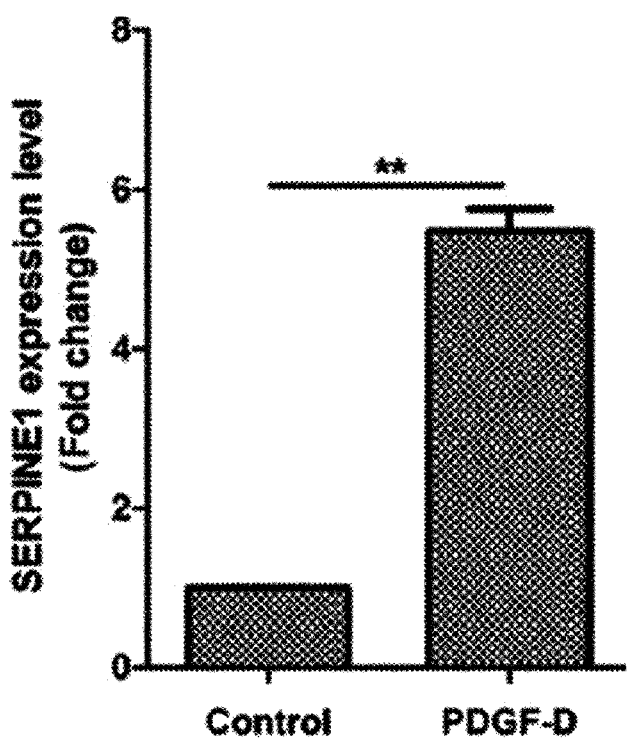
Figure 6E:
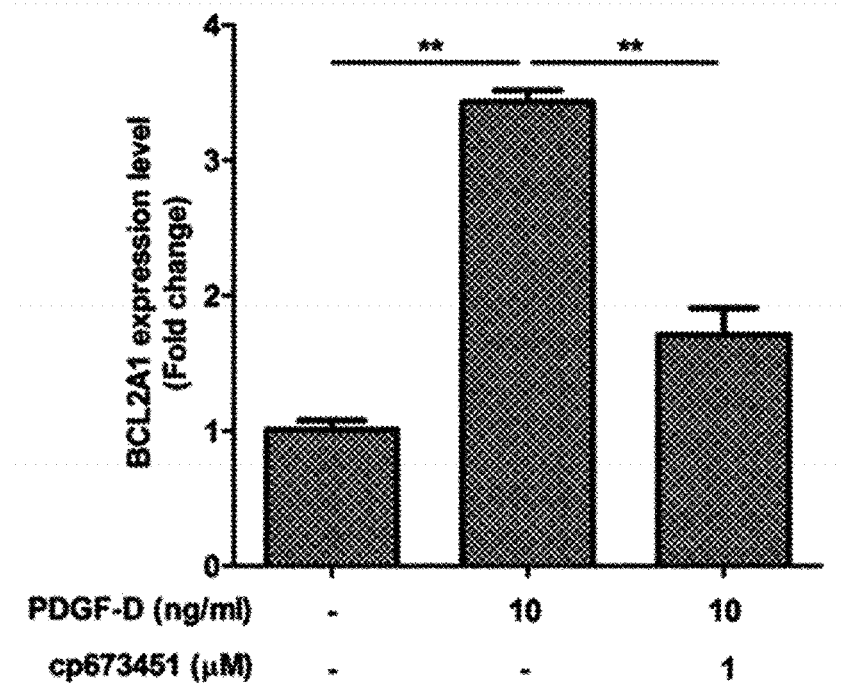
Figure 6F:
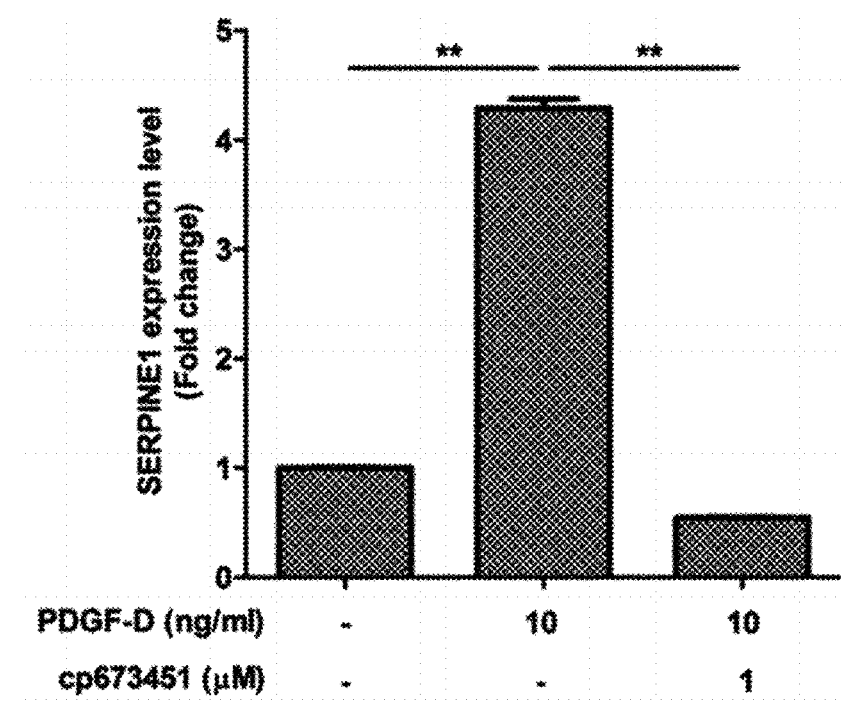

As a result, BCL2A1 mRNA expression was increased in ASCs 4 hours after the PDGF-D treatment (FIG. 6A), and SERPINE1 mRNA expression was increased 24 hours after the treatment (FIG. 6C). In addition, the increase of BCL2A1 and SERPINE1 expression was reconfirmed by qPCR (FIGS. 6B, 6D). In addition, it was confirmed that the BCL2A1 and SERPINE1 expression was decreased in ASCs by the treatment of PDGFR-β inhibitor cp673451 (FIGS. 6E, 6F).

Afterward, the ASC proliferation and migration induced by PDGF-D were examined after transfecting siRNA (Dharmacon, USA) of BCL2A1 and SERPINE1 in ASCs for 48 hours using lipofectamine 2000 (Invitrogen).

Figure 7A:
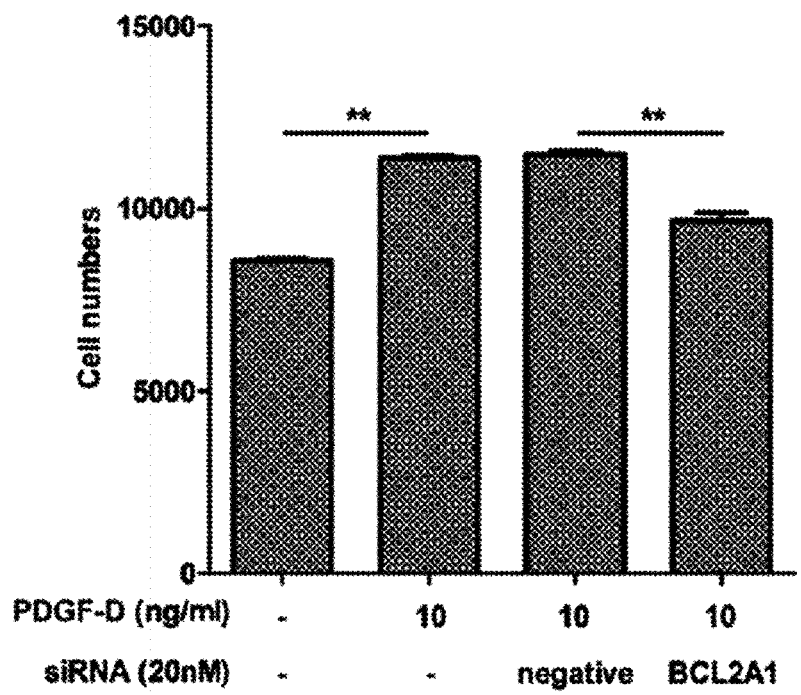
FIG. 7A shows cell numbers against treatment of BCL2A1 siRNA in ASCs.
Figure 7B:
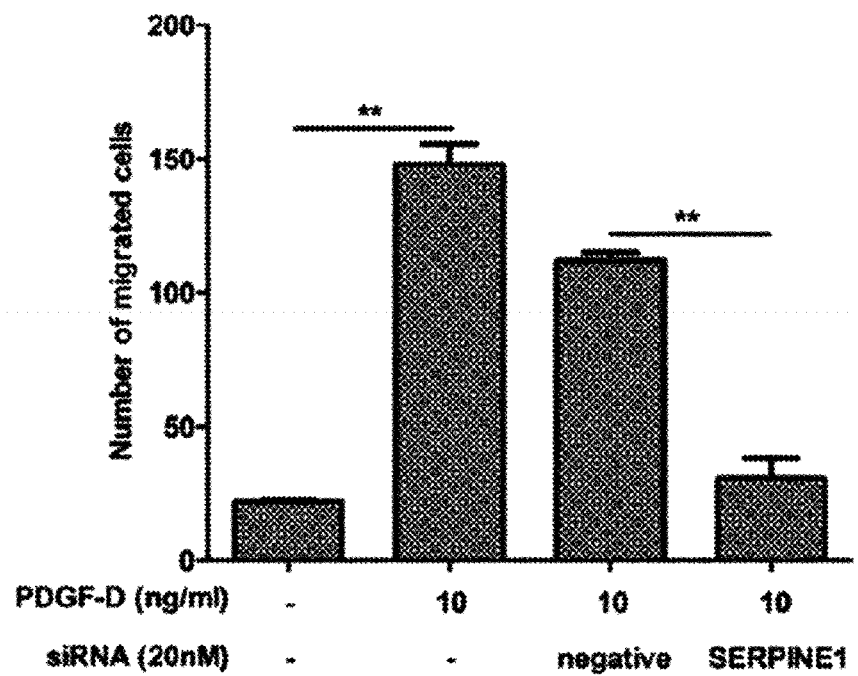
FIG. 7B shows cell migration against treatment of SERPINE1 siRNA.
Figure 7C:
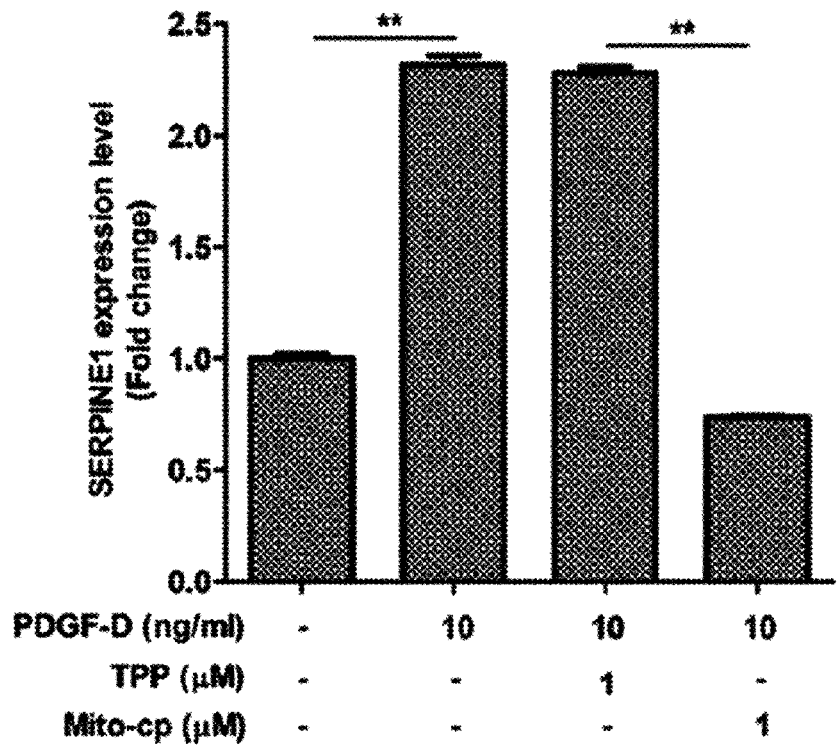
FIG. 7C shows SERPINE1 expression against treatment of inhibitor for mitochondrial ROS generation.
Figure 7D:
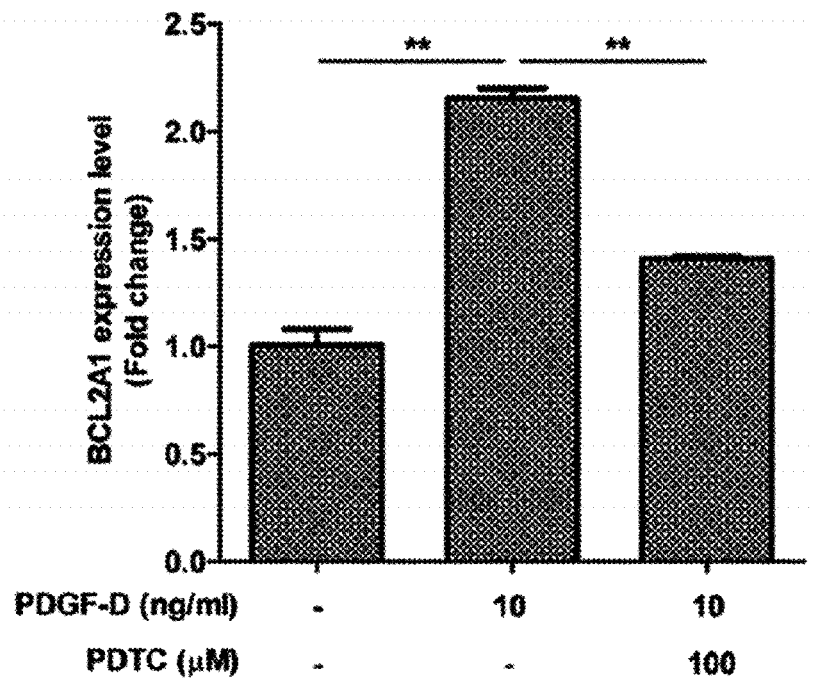
FIG. 7D shows BCL2A1 expression against inhibition of the NF-κB pathway.

As a result, while the ASC proliferation was slightly decreased by BCL2A1 siRNA (FIG. 7A), the ASC migration was considerably decreased by SERPINE1 siRNA (FIG. 7B). In addition, the inhibitor for mitochondrial ROS generation Mito-CP had no influence on the BCL2A1 mRNA expression and considerably decreased the SERPINE1 mRNA expression (FIG. 7C). This means that cell migration induced by PDGF-D in ASCs was mediated by SERPINE1, and mitochondrial ROS generation regulated SERPINE1 mRNA transcription. BCL2A1 expression was decreased by an inhibitor for the NF-κB pathway, PDTC (FIG. 7D).

Example 6 Promotion of Hair Growth of PDGF-D-Pretreated ASCs

In this example, it was confirmed that hair regenerative potential was increased by pretreating ASCs with PDGF-D.

Mice were maintained and anesthetized according to a protocol approved by the United States Pharmacopoeia (USP) and the Institutional Animal Care and Use Committee of CHA University (IACUC120002).

7-week-old C3H/HeN mice, that is, telogen-to-anagen transition model in a telogen stage of the hair cycle, were shaved, and then 1×10$^4$ of ASCs and FBS-free ASCs pretreated with 10 ng/ml of PDGF-D for 24 hours were injected into the mice (Kim et al., *Stem Cells Dev* 23:1364-1376, 2014). Skin darkening (that indicates hair cycle induction) was monitored, and after 15 days, the hair on the back of the mouse was shaved, and the weight of the mouse was measured.

Figure 8A:
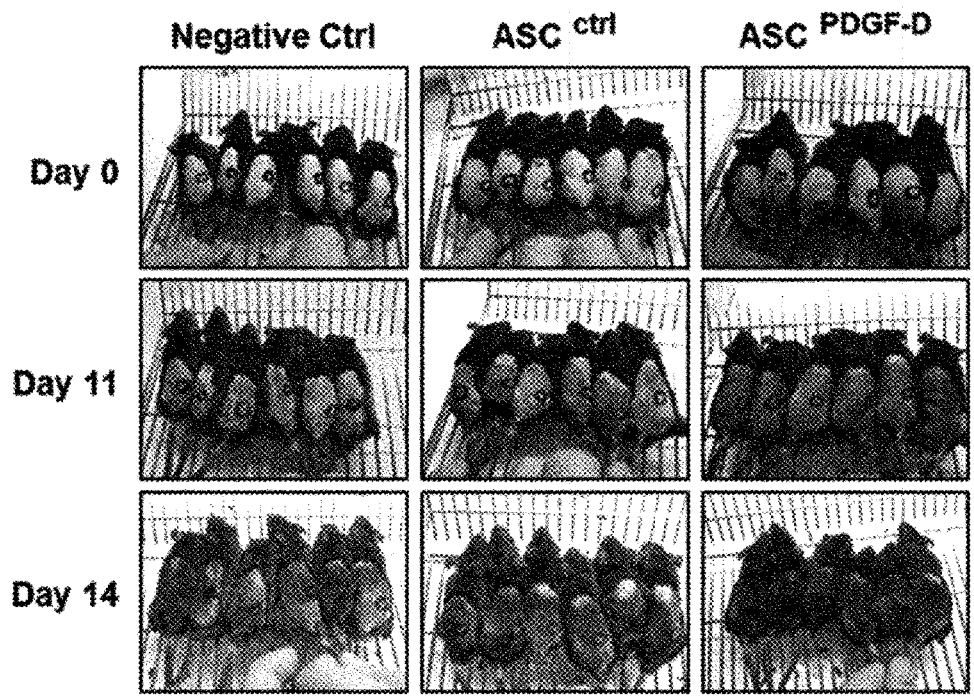
FIGS. 8A to 8D show the expression of growth factors and the increase of hair regenerative potential in ASCs by PDGF-D treatment (FIG. 8A: hair regeneration by PDGF-D-treated ASCs.
Figure 8B:
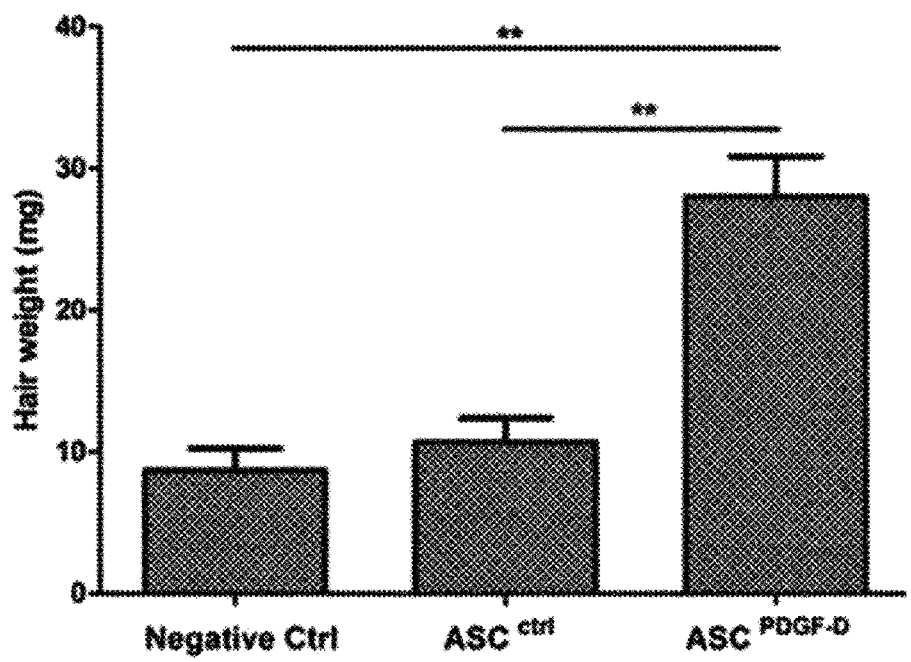

As a result, it can be confirmed that, compared with controls, (negative control and ASC only-treated control), PDGF-D-pretreated ASCs were injected into the mice, and on day 14, hair growth was considerably increased and the back of the mouse was covered by the hair. The anagen induction of the hair was not limited to cell-injected parts, skin darkening or hair regeneration occurred on all parts (FIG. 8A). In addition, a hair weight measured on day 14 was considerably increased, three times or more, in the PDGF-D-pretreated ASC group (FIG. 8B).

Figure 8C:
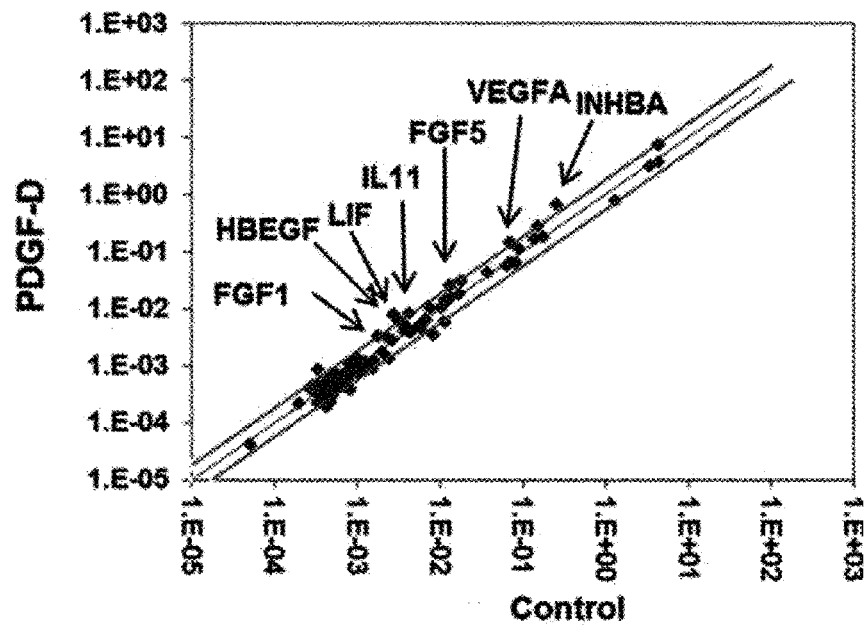
Figure 8D:
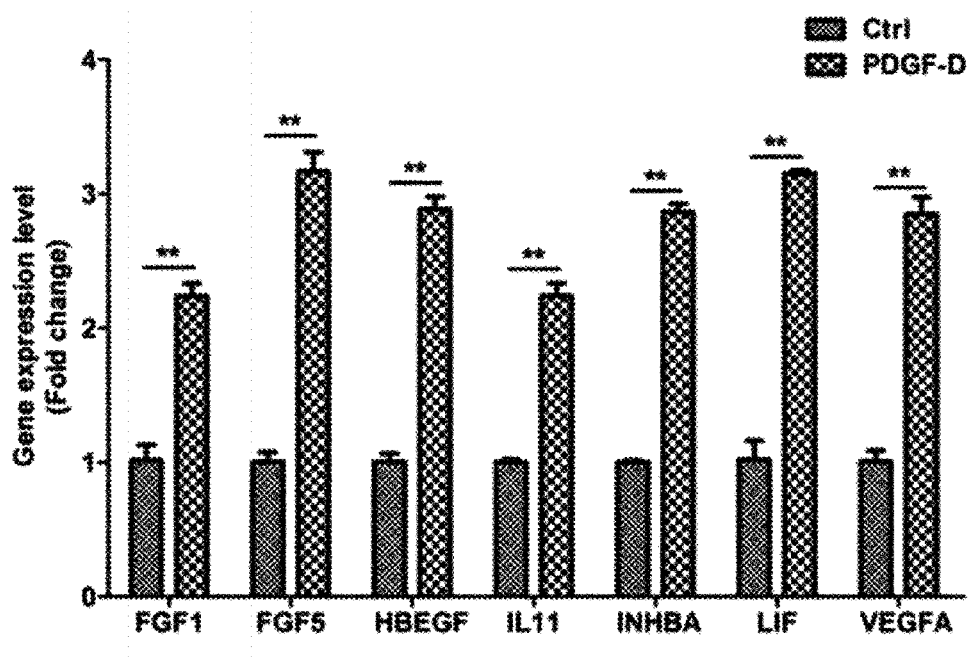

Then, the paracrine effect of PDGF families was examined using an RT$^2$ profiler PCR array of a human growth factor (growth factor pathway: PAHS-041ZA). As a result, PDGF-D increased the expression of growth factors such as VEGFA, FGF1, FGF5, BMP8B, LIF, INHBA, IL11 and HBEGF (>1.8-fold) (FIG. 8C), and the increased expression of VEGFA, FGF1, FGF5, LIF, INHBA, IL11 and HBEGF was detected by qPCR (FIG. 8D).

Example 7 Increase of Growth Factor Expression Through MAPK Pathway

In this example, after PDGF-D treatment, the increase of growth factor expression through a signaling pathway and a transcription factor of the growth factor were investigated.

Since ROS generation and inhibition of the PI3K/Akt pathway did not decrease the growth factor expression, the expression of a growth factor induced by PDGF-D was inhibited instead by the treatment of 10 μM of an inhibitor for the MARK pathway U0126 (Clbiochem). The growth factor expression was measured by an RT$^2$ profiler PCR array (FIG. 9A). In addition, the fact that inhibition of the MAPK pathway by the U0126 inhibitor inhibited the expression of the growth factor induced by PDGF-D was reconfirmed using qPCR (FIG. 9B).

PDGF-D-treated ASCs according to embodiments of the present invention are increased in hair regenerative potential due to increases of proliferation, migration and secretion of growth factors, and thus are useful for a therapeutic agent for hair loss or a cosmetic for preventing hair loss.

The PDGF-D-treated ASCs according to embodiments of the present invention have considerably increased growth/proliferation potential when culturing and dramatically decreased production cost as well as culture period.

The PDGF-D-treated ASCs according to embodiments of the present invention is a cellular therapeutic agent for hair loss which is potent evidence supporting the latest theory that a low concentration of ROS acts as an intracellular signal transduction substance to promote cell growth.

According to embodiments of the present invention, the hair growing and skin regenerating effects of ASCs were identified using phase-transition animal models (animal model in which the hair cycle transitions from telogen to anagen), and when PDGF-D-pretreated ASCs were subcutaneously injected, compared with a negative control and an ASC only-treated group, considerable induction of hair in anagen and hair growth were detected.

From above, specific parts of the present invention have been described in detail. However, it will be apparent to those of ordinary skill in the art that such detailed descriptions are just embodiments, and thus the scope of the present invention is not limited thereto. Therefore, the actual range of the present invention will be defined by the accompanying claims and equivalents thereof. Simple modifications or alternations of the present invention can be easily used by those of ordinary skill in the art, and it should be apparent that all of such modifications and alternations are included in the scope of the present invention.

What is claimed is:

1. A method for proliferating stem cells, comprising: culturing adipose-derived stem cells in a platelet-derived growth factor-D (PDGF-D)-added medium.

2. The method of claim 1, wherein the concentration of PDGF-D is 1 to 50 ng/ml.

3. The method of claim 1, wherein the adipose-derived stem cells have one or more of the following characteristics:
   i) an increased level of Akt or ERK phosphorylation;
   ii) increased generation of reactive oxygen species;
   iii) induction of mitochondrial fission; and
   iv) increased growth factor expression or secretion.

4. The method of claim 3, wherein the growth factor is one or more selected from the group consisting of vascular endothelial growth factor A (VEGFA), fibroblast growth factor 1 (FGF1), fibroblast growth factor 5 (FGF5), bone morphogenetic protein 8B (BMP8B), leukocyte migration inhibitory factor (LIF), inhibin beta A (INHBA), interleukin 11 (IL11) and heparin-binding EGF-like growth factor (HBEGF).

5. A method for promoting hair growth, comprising:
   culturing adipose-derived stem cells in a platelet-derived growth factor-D (PDGF-D)-added medium;
   collecting at least part of the adipose-derived stem cells or the culture medium; and
   administering a composition comprising the adipose-derived stem cells or the culture medium thereof to a subject.

6. The method of claim 5, wherein the adipose-derived stem cells are derived from a fat.

* * * * *